United States Patent
Nishioka et al.

(10) Patent No.: US 11,523,788 B2
(45) Date of Patent: Dec. 13, 2022

(54) MEDICAL INFORMATION PROCESSING APPARATUS, MEDICAL INFORMATION PROCESSING SYSTEM, AND MEDICAL INFORMATION PROCESSING METHOD

(71) Applicant: CANON MEDICAL SYSTEMS CORPORATION, Otawara (JP)

(72) Inventors: Takahiko Nishioka, Otawara (JP); Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 22 days.

(21) Appl. No.: 16/238,545

(22) Filed: Jan. 3, 2019

(65) Prior Publication Data
US 2019/0209114 A1    Jul. 11, 2019

(30) Foreign Application Priority Data

Jan. 11, 2018 (JP) .............................. JP2018-002974
Dec. 7, 2018 (JP) .............................. JP2018-229681

(51) Int. Cl.
*A61B 6/00* (2006.01)
*A61B 6/03* (2006.01)
*G06T 7/00* (2017.01)

(52) U.S. Cl.
CPC .............. *A61B 6/504* (2013.01); *A61B 6/032* (2013.01); *A61B 6/5217* (2013.01); *G06T 7/0012* (2013.01); *G06T 2207/10081* (2013.01); *G06T 2207/30104* (2013.01)

(58) Field of Classification Search
None
See application file for complete search history.

(56) References Cited

U.S. PATENT DOCUMENTS

2011/0103666 A1*  5/2011  Ohishi .................. G06T 19/003
                                                  382/131
2012/0041318 A1    2/2012  Taylor
2012/0041319 A1    2/2012  Taylor et al.
(Continued)

FOREIGN PATENT DOCUMENTS

JP    2011-115562 A    6/2011
JP    2013-534154      9/2013
(Continued)

OTHER PUBLICATIONS

Brian S., Ko, et al., "Noninvasive CT-Derived FFR Based on Structural and Fluid Analysis", JACC: Cardiovascular Imaging, vol. 10, No. 6, 2017, 11 pages.
(Continued)

*Primary Examiner* — Delomia L Gilliard
(74) *Attorney, Agent, or Firm* — Oblon, McClelland, Maier & Neustadt, L.L.P.

(57) ABSTRACT

A medical information processing apparatus includes processing circuitry. The processing circuitry is configured to acquire medical image data representing a blood vessel of a subject, extract a blood vessel shape from the medical image data, determine degree of meandering in each of regions from the extracted blood vessel shape, specify a deformed region in which the degree of meandering changes due to insertion of a device into the blood vessel on the basis of the degree of meandering, and output the deformed region in the blood vessel.

18 Claims, 9 Drawing Sheets

BEFORE DEVICE INSERTION

AFTER DEVICE INSERTION

(56) References Cited

U.S. PATENT DOCUMENTS

| | | |
|---|---|---|
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0150516 A1 | 6/2012 | Taylor et al. |
| 2013/0054214 A1 | 2/2013 | Taylor |
| 2013/0064438 A1 | 3/2013 | Taylor et al. |
| 2013/0066618 A1 | 3/2013 | Taylor et al. |
| 2013/0151163 A1 | 6/2013 | Taylor et al. |
| 2013/0211728 A1 | 8/2013 | Taylor et al. |
| 2014/0107935 A1 | 4/2014 | Taylor |
| 2014/0148693 A1 | 5/2014 | Taylor |
| 2014/0155770 A1 | 6/2014 | Taylor |
| 2014/0200867 A1 | 7/2014 | Lavi et al. |
| 2014/0207432 A1 | 7/2014 | Taylor |
| 2014/0222406 A1 | 8/2014 | Taylor |
| 2014/0236492 A1 | 8/2014 | Taylor |
| 2014/0243663 A1 | 8/2014 | Taylor |
| 2014/0247970 A1 | 9/2014 | Taylor |
| 2014/0249791 A1 | 9/2014 | Taylor |
| 2014/0249792 A1 | 9/2014 | Taylor |
| 2014/0348412 A1 | 11/2014 | Taylor |
| 2014/0355859 A1 | 12/2014 | Taylor et al. |
| 2015/0005615 A1* | 1/2015 | Inoue ................. A61B 5/1128 600/407 |
| 2015/0038860 A1* | 2/2015 | Fonte ................. A61B 5/026 600/505 |
| 2015/0073722 A1 | 3/2015 | Taylor et al. |
| 2015/0088015 A1 | 3/2015 | Taylor |
| 2015/0088478 A1 | 3/2015 | Taylor |
| 2015/0150530 A1 | 6/2015 | Taylor et al. |
| 2015/0161326 A1 | 6/2015 | Taylor et al. |
| 2015/0161348 A1 | 6/2015 | Taylor et al. |
| 2015/0161790 A1* | 6/2015 | Takahashi ............ A61B 6/504 600/424 |
| 2015/0201849 A1 | 7/2015 | Taylor |
| 2015/0257655 A1* | 9/2015 | Ishii ................... A61B 6/032 600/508 |
| 2015/0332015 A1 | 11/2015 | Taylor |
| 2015/0335304 A1 | 11/2015 | Lavi et al. |
| 2015/0339459 A1 | 11/2015 | Taylor |
| 2015/0363941 A1 | 12/2015 | Taylor |
| 2015/0379230 A1 | 12/2015 | Taylor |
| 2016/0007945 A1 | 1/2016 | Taylor |
| 2016/0073991 A1 | 3/2016 | Taylor |
| 2016/0110517 A1 | 4/2016 | Taylor |
| 2016/0110866 A1 | 4/2016 | Taylor |
| 2016/0110867 A1 | 4/2016 | Taylor |
| 2016/0113528 A1 | 4/2016 | Taylor |
| 2016/0113726 A1 | 4/2016 | Taylor |
| 2016/0117815 A1 | 4/2016 | Taylor |
| 2016/0117816 A1 | 4/2016 | Taylor |
| 2016/0117819 A1 | 4/2016 | Taylor |
| 2016/0128661 A1 | 5/2016 | Taylor |
| 2016/0133015 A1 | 5/2016 | Taylor |
| 2016/0135787 A1* | 5/2016 | Anderson ............ A61B 8/463 600/407 |
| 2016/0140313 A1 | 5/2016 | Taylor |
| 2016/0232667 A1 | 8/2016 | Taylor |
| 2016/0246939 A1 | 8/2016 | Taylor |
| 2016/0296287 A1 | 10/2016 | Taylor |
| 2016/0364859 A1 | 12/2016 | Taylor |
| 2016/0364860 A1 | 12/2016 | Taylor |
| 2016/0364861 A1 | 12/2016 | Taylor |
| 2016/0371455 A1 | 12/2016 | Taylor |
| 2017/0053092 A1 | 2/2017 | Taylor |
| 2017/0105694 A1* | 4/2017 | Grass ................. A61B 6/507 |
| 2017/0202621 A1 | 7/2017 | Taylor |
| 2017/0227620 A1* | 8/2017 | Wakai ................ A61B 5/0044 |
| 2017/0340392 A1 | 11/2017 | Taylor |
| 2017/0364658 A1 | 12/2017 | Lavi et al. |
| 2018/0071027 A1 | 3/2018 | Taylor |
| 2018/0092615 A1* | 4/2018 | Sakaguchi ........... A61B 5/004 |
| 2018/0092616 A1* | 4/2018 | Sakaguchi ........... G06T 7/0016 |
| 2018/0161099 A1* | 6/2018 | Dumenil ............. A61B 6/488 |
| 2018/0161104 A1 | 6/2018 | Taylor |
| 2018/0268941 A1 | 9/2018 | Lavi et al. |
| 2018/0286045 A1* | 10/2018 | Hansis ................ G16H 30/40 |
| 2018/0330503 A1* | 11/2018 | Hoi .................... G06T 7/0016 |

FOREIGN PATENT DOCUMENTS

| | | |
|---|---|---|
| JP | 2014-108208 A | 6/2014 |
| JP | 2016-509501 | 3/2016 |
| WO | WO 2016/207358 A1 | 12/2016 |

OTHER PUBLICATIONS

Sinichiro Fujimoto, et al., "Diagnostic performance of on-site computed CT-fractional flow reserve based on fluid structure interactions comparison with invasive fractional flow reserve and instantaneous wave-free ratio", European Heart Journal—Cariovascular Imaging, 2018, 10 pages.

English translation of International Search Report dated Apr. 9, 2019, in PCT/JP2019/000406, 1 page.

Notification of Reasons for Refusal dated Jun. 21, 2022, in Japanese Patent Application No. 2018-229681.

* cited by examiner

MEDICAL INFORMATION PROCESSING APPARATUS, MEDICAL INFORMATION PROCESSING SYSTEM, AND MEDICAL INFORMATION PROCESSING METHOD

CROSS-REFERENCE TO RELATED APPLICATIONS

This application is based upon and claims the benefit of priority from Japanese Patent Application No. 2018-2974, filed on Jan. 11, 2018; and Japanese Patent Application No. 2018-229681, filed on Dec. 7, 2018, the entire contents of which are incorporated herein by reference.

FIELD

Embodiments described herein relate generally to a medical information processing apparatus, a method information processing system, and a medical information processing method.

BACKGROUND

As a method for acquiring an index (fluid index) relating to a blood flow of a subject, known methods include a method of measuring the index with a device inserted into a blood vessel, and a method of calculating the index from medical image data in which the blood vessel of the subject is represented. However, the fluid indexes acquired from these methods may deviate from each other.

DETAILED DESCRIPTION

A medical information processing apparatus comprises processing circuitry. The processing circuitry is configured to acquire medical image data representing a blood vessel of a subject. The processing circuitry is configured to extract a blood vessel shape from the medical image data, determine degree of meandering in each of regions from the extracted blood vessel shape, and specify a deformed region in which the degree of meandering changes due to insertion of a device into the blood vessel on the basis of the degree of meandering. And the processing circuitry is configured to output the deformed region in the blood vessel.

The following is a detailed explanation of embodiments of the medical information processing apparatus, a medical information processing system, and a medical information processing method with reference to drawings.

First, the following is an explanation of a first embodiment. The first embodiment illustrates a medical information processing system 1 including a medical image diagnostic apparatus 10 and a medical information processing apparatus 30, as an example.

Figure 1:
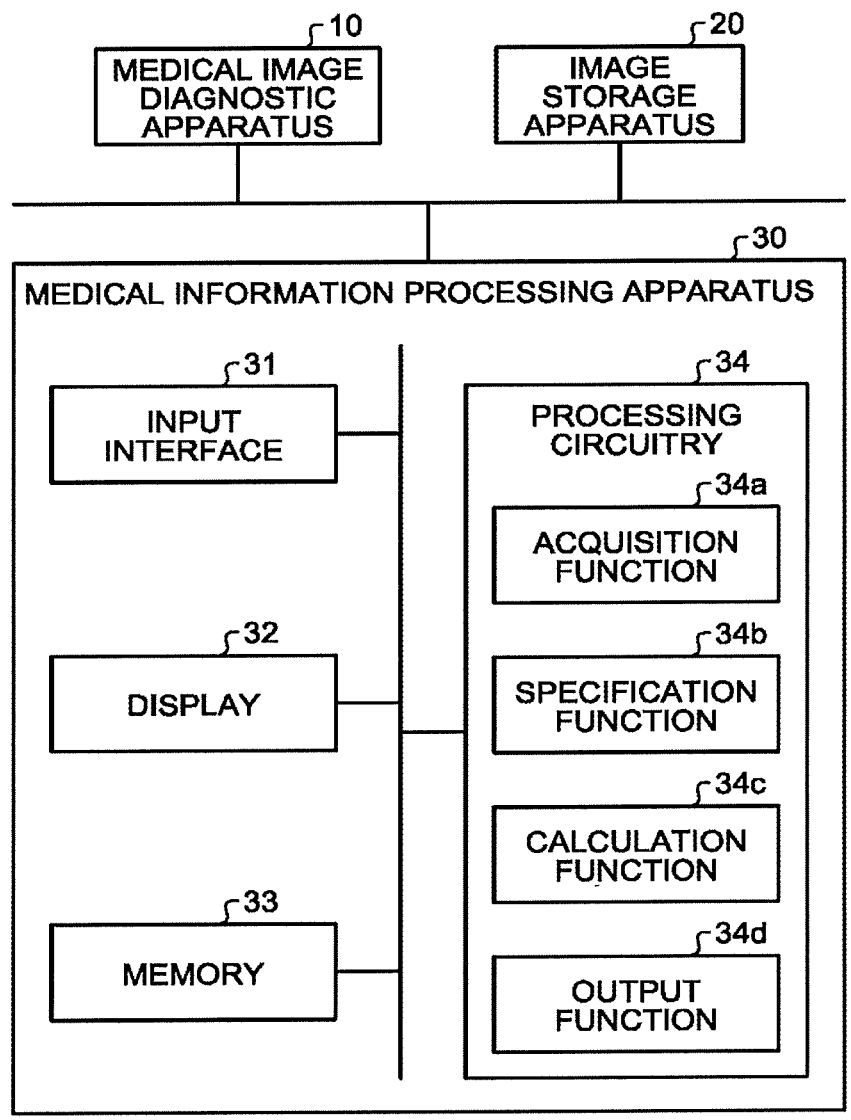
FIG. 1 is a block diagram illustrating an example of configuration of a medical information processing system according to a first embodiment.

As illustrated in FIG. 1, the medical information processing system 1 according to the first embodiment includes the medical image diagnostic apparatus 10, an image storage apparatus 20, and the medical information processing apparatus 30. FIG. 1 is a diagram illustrating an example of configuration of the medical information processing system 1 according to the first embodiment. As illustrated in FIG. 1, the medical image diagnostic apparatus 10, the image storage apparatus 20, and the medical information processing apparatus 30 are mutually connected through a network.

The medical image diagnostic apparatus 10 is an apparatus acquiring medical image data from a subject P. The medical image diagnostic apparatus 10 acquires medical image data in which a blood vessel of the subject P is represented, and transmits the acquired medical image data to the image storage apparatus 20 and the medical information processing apparatus 30. For example, the medical image diagnostic apparatus 10 is an X-ray computed tomography (CT) apparatus, an X-ray diagnostic apparatus, a magnetic resonance imaging (MRI) apparatus, or the like.

The image storage apparatus 20 is an apparatus storing therein medical image data acquired with the medical image diagnostic apparatus 10. The image storage apparatus 20 acquires medical image data from the medical image diagnostic apparatus 10 through the network, and stores the acquired medical image data in a memory provided inside or outside thereof. For example, the image storage apparatus 20 is achieved with a computer apparatus, such as a server apparatus.

The medical information processing apparatus 30 acquires medical image data through the network, and executes various types of processing using the acquired medical image data. For example, the medical information processing apparatus 30 acquires medical image data from the medical image diagnostic apparatus 10 or the image storage apparatus 20 through the network. The medical information processing apparatus 30 also specifies a deformed region described later on the basis of the acquired medical image data, and outputs the specified deformed region. For example, the medical information processing apparatus 30 is achieved with a computer apparatus, such as a workstation. The medical image diagnostic apparatus 10, the image storage apparatus 20, and the medical information processing apparatus 30 may be installed in any places, as long as they can be mutually connected through a network. For example, the medical information processing apparatus 30 may be installed in a hospital different from a hospital in which the medical image diagnostic apparatus 10 is installed.

As illustrated in FIG. 1, the medical information processing apparatus 30 includes an input interface 31, a display 32, a memory 33, and processing circuitry 34.

The input interface 31 receives various input operations from an operator, converts the received input operation into an electrical signal, and outputs the electrical signal to the processing circuitry 34. For example, the input interface 31 is achieved with a mouse, a keyboard, a trackball, a switch, a button, a joystick, a touch pad to perform an input operation by a touch on an operation surface thereof, a touch screen in which a display screen is united with a touch pad, a non-contact input circuit using an optical sensor, a sound input circuit, or the like. The input interface 31 may be formed of a tablet terminal or the like capable of performing wireless communications with the main member of the medical information processing apparatus 30. The input interface 31 is not limited to a structure including physical operation components, such as a mouse and a keyboard. For example, examples of the input interface 31 also include an electrical signal processing circuit receiving an electrical signal corresponding to an input operation from an external input device provided separately from the medical information processing apparatus 30, and outputting the electrical signal to the processing circuitry 34.

The display 32 displays various types of information. For example, the display 32 displays a deformed region specified with the processing circuitry 34 and/or a fluid index calculated with the processing circuitry 34, under the control of the processing circuitry 34. The display 32 also displays a graphical user interface (GUI) to receive various instructions and/or various settings from the operator through the input interface 31. For example, the display 32 is a liquid crystal display or a cathode ray tube (CRT) display. The display 32 may be of a desktop type, or may be formed of a tablet terminal or the like capable of performing wireless communications with the main member of the medical information processing apparatus 30.

The memory 33 is achieved with a semiconductor memory device, such as a random access memory (RAM) and a flash memory, a hard disk, an optical disk, or the like. For example, the memory 33 stores therein medical image data acquired from the medical image diagnostic apparatus 10 or the image storage apparatus 20. For example, the memory 33 stores therein a computer program to cause the circuit included in the medical information processing apparatus 30 to achieve its function.

The processing circuitry 34 executes an acquisition function 34a, a specification function 34b, a calculation function 34c, and an output function 34d, to control operations of the whole medical information processing apparatus 30. The acquisition function 34a is an example of the acquirer. The specification function 34b is an example of the specifier. The calculation function 34c is an example of the calculator. The output function 34d is an example of the outputer.

For example, the processing circuitry 34 reads a computer program corresponding to the acquisition function 34a from the memory 33 and executes the computer program to acquire medical image data, in which the blood vessel of the subject P is represented, from the medical image diagnostic apparatus 10 or the image storage apparatus 20. For example, the processing circuitry 34 reads a computer program corresponding to the specification function 34b from the memory 33 and executes the computer program to extract the shape of the blood vessel from the medical image data, determine the degree of meandering in each of regions from the extracted shape of the blood vessel, and specify the deformed region on the basis of the degree of meandering. For example, the processing circuitry 34 reads a computer program corresponding to the calculation function 34c from the memory 33 and executes the computer program to calculate the fluid index in the blood vessel of the subject P. For example, the processing circuitry 34 reads a computer program corresponding to the output function 34d from the memory 33 and executes the computer program to output the deformed region in association with the fluid index in the blood vessel of the subject P.

In the medical information processing apparatus 30 illustrated in FIG. 1, each of the processing functions is stored in the form of a computer program executable with a computer in the memory 33. The processing circuitry 34 is a processor reading a computer program from the memory 33 and executing the computer program to achieve the function corresponding to the computer program. In other words, the processing circuitry 34 in a state of reading each computer program has a function corresponding to the read computer program. FIG. 1 illustrates that the single processing circuitry 34 achieves the acquisition function 34a, the specification function 34b, the calculation function 34c, and the output function 34d, but a plurality of independent processors may be combined to form the processing circuitry 34, and the functions may be achieved by executing the computer programs with the processors.

The following is an explanation of the medical image diagnostic apparatus 10 acquiring medical image data in which the blood vessel of the subject P is represented. The present embodiment illustrates an X-ray CT apparatus 100 as an example of the medical image diagnostic apparatus 10. The present embodiment also illustrates CT image data (volume data) as an example of the medical image data.

Figure 2:
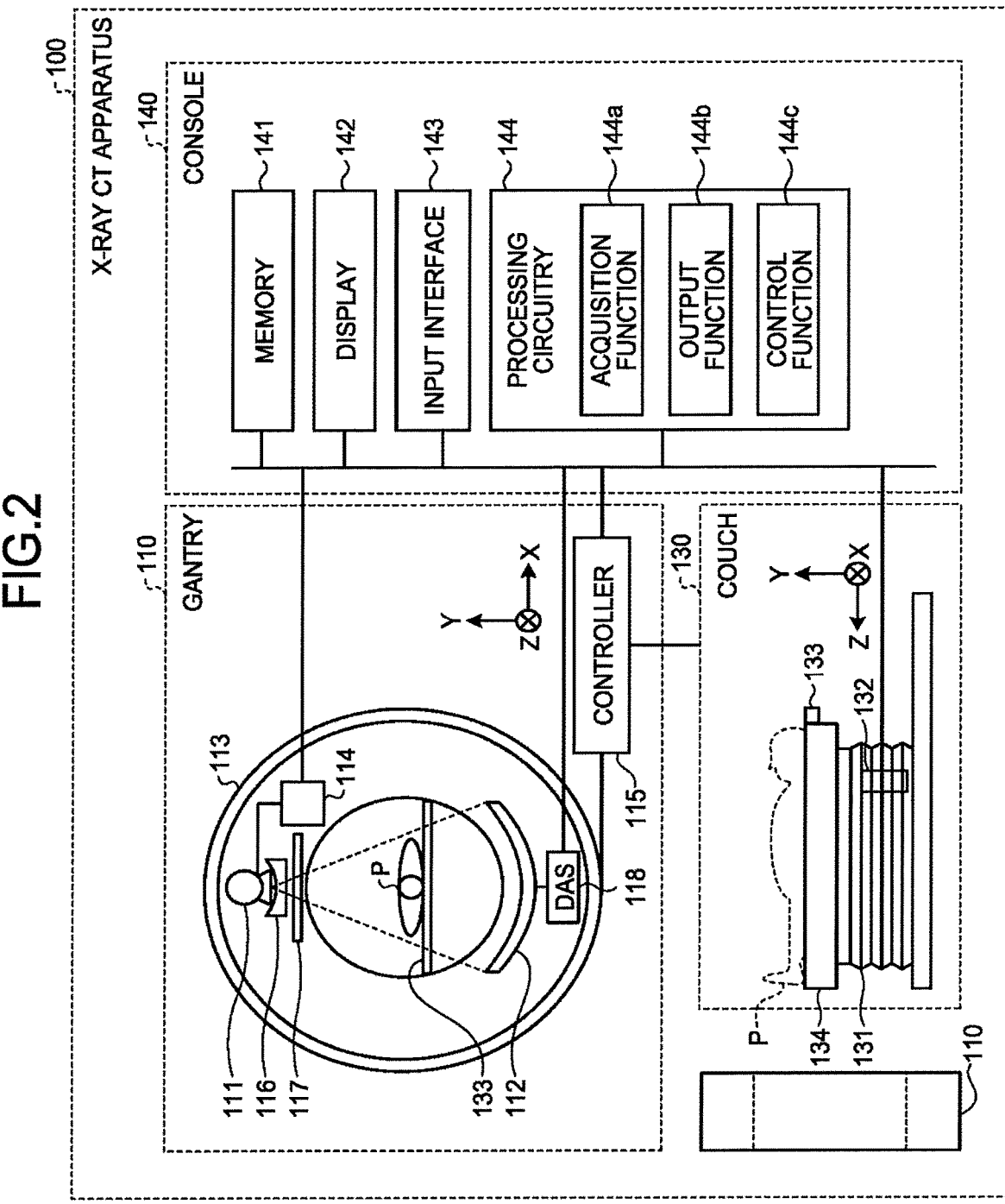
FIG. 2 is a block diagram illustrating an example of configuration of an X-ray CT apparatus according to the first embodiment.

As illustrated in FIG. 2, the X-ray CT apparatus 100 includes a gantry 110, a couch 130, and a console 140. FIG. 2 is a block diagram illustrating an example of configuration of the X-ray CT apparatus 100 according to the first embodiment. In FIG. 2, a Z-axis direction is a longitudinal direction of a rotational axis of a rotary frame 113 in a non-tilt state or a tabletop 133 of the couch 130. An X-axis direction is an axial direction orthogonal to the Z-axis direction and horizontal to the floor surface. A Y-axis direction is an axial direction orthogonal to the Z-axis direction and perpendicular to the floor surface. FIG. 2 illustrates the gantry 110 in a plurality of directions for explanation, and illustrates the case where the X-ray CT apparatus 100 includes one gantry 110.

The gantry 110 includes an X-ray tube 111, an X-ray detector 112, a rotary frame 113, an X-ray high-voltage device 114, a controller 115, a wedge 116, a collimator 117, and a data acquisition system (DAS) 118.

The X-ray tube 111 is a vacuum tube including a cathode (filament) generating thermoelectrons and an anode (target) suffering collision of thermoelectrons to generate X-rays. In the X-ray tube 111, thermoelectrons are radiated from the cathode to the anode by application of high voltage from the X-ray high-voltage device 114, to generate X-rays.

The X-ray detector 112 detects X-rays radiated from the X-ray tube 111 and transmitted through the subject P, and outputs a signal corresponding to the detected X-ray quantity to the DAS 118. The X-ray detector 112 includes, for example, a plurality of X-ray detection element lines, in each of which a plurality of X-ray detection elements are arranged in a channel direction along an arc with the focus of the X-ray tube 111 serving as the center. For example, the X-ray detector 112 has a structure in which a plurality of X-ray detection element lines, in each of which a plurality of X-ray detection elements are arranged in a channel direction, are arranged in a slice direction (the row direction). The X-ray detector 112 is, for example, an indirect-conversion detector including a grid, a scintillator array, and an optical sensor array. The scintillator array includes a plurality of scintillators. Each of the scintillators includes a scintillator crystal outputting light of a photon quantity corresponding to the incident X-ray quantity. The grid is disposed on an X-ray incident surface of the scintillator array, and includes an X-ray shield plate absorbing scattered X-rays. The grid may be referred to as a collimator (one-dimensional collimator or two-dimensional collimator). The optical sensor array has a function of converting the light into an electrical signal corresponding to the light quantity from the scintillator, and includes an optical sensor, such as a photo multiplier (PMT). The X-ray detector 112 may be a direct-conversion detector including semiconductor devices converting the incident X-rays into electrical signals.

The rotary frame 113 is an annular frame supporting the X-ray tube 111 and the X-ray detector 112 such that they are opposed to each other, and rotating the X-ray tube 111 and the X-ray detector 112 with the controller 115. For example, the rotary frame 113 is a casting formed of aluminum. The rotary frame 113 may also support the X-ray high-voltage device 114 and/or the DAS 118, in addition to the X-ray tube 111 and the X-ray detector 112. The rotary frame 113 may also support various structures not illustrated in FIG. 2. In the following explanation, the part rotating and moving together with the rotary frame 113 and the rotary frame 113 are also referred to as a "rotary unit" in the gantry 110.

The detection data generated with the DAS 118 is transmitted from a transmitter provided on the rotary frame 113 and including a light emitting diode (LED) to a receiver provided on a non-rotating portion of the gantry 110 and including a photodiode by optical communication, and transferred to the console 140. The non-rotating portion is, for example, a fixed frame or the like rotatably supporting the rotary frame 113. The method for transmitting detection data from the rotary frame 113 to the gantry 110 is not limited to optical communication, but any method may be adopted as long as it is non-contact data transmission.

The X-ray high-voltage device 114 includes a high-voltage generator including an electrical circuit, such as a transformer and a rectifier, and generating high voltage to be applied to the X-ray tube 111, and an X-ray controller controlling the output voltage corresponding to X-rays radiated from the X-ray tube 111. The high-voltage generator may be of a transformer type or an inverter type. The X-ray high-voltage device 114 may be provided on the rotary frame 113, or provided on a fixed frame (not illustrated).

The controller 115 includes a processing circuit including a central processing unit (CPU), and a drive mechanism, such as a motor and an actuator. The controller 115 receives an input signal from an input interface 143, and controls operations of the gantry 110 and the couch 130. For example, the controller 115 performs control on rotation of the rotary frame 113, tilt of the gantry 110, and operations of the couch 130 and the tabletop 133, and like. As an example, the controller 115 rotates the rotary frame 113 with an axis parallel with the X-axis direction serving as a center, with input inclination angle (tilt angle) information, as control to tilt the gantry 110. The controller 115 may be provided on the gantry 110, or provided on the console 140.

The wedge 116 is a filter to regulate the X-ray quantity radiated from the X-ray tube 111. Specifically, the wedge 116 is a filter transmitting and attenuating the X-rays radiated from the X-ray tube 111 such that the X-rays radiated from the X-ray tube 111 to the subject P has predetermined distribution. For example, the wedge 116 is a wedge filter or a bow-tie filter, and formed by processing aluminum or the like to have a predetermined target angle and/or a predetermined thickness.

The collimator 117 is a lead plate or the like to narrow down the irradiation range of the X-rays transmitted through the wedge 116, and forms a slit with a combination of a plurality of lead plates and the like. The aperture and the position of the collimator 117 are regulated with a collimator regulation circuit (not illustrated). This structure regulates the irradiation range of the X-rays generated with the X-ray tube 111. The collimator 117 is also referred to as an "X-ray diaphragm".

The DAS 118 includes an amplifier performing amplification on the electrical signal output from each of the X-ray detection elements of the X-ray detector 112, and an A/D converter converting the electrical signal into a digital signal, and generates detection data. The DAS 118 is achieved with, for example, a processor.

The couch 130 is a device to place and move the subject P serving as a scan target. The couch 130 includes a base 131, a couch drive device 132, the tabletop 133, and a support frame 134. The base 131 is a housing supporting the support frame 134 to be movable in the vertical direction. The couch drive device 132 is a drive mechanism moving the tabletop 133 on which the subject P is placed in a long-axis direction of the tabletop 133, and includes a motor and an actuator. The tabletop 133 provided on the upper surface of the support frame 134 is a plate on which the subject P is placed. The couch drive device 132 may move the support frame 134 in the long-axis direction of the tabletop 133, in addition to the tabletop 133.

The console 140 includes a memory 141, a display 142, the input interface 143, and processing circuitry 144.

The memory 141 is achieved with, for example, a semiconductor memory, such as a RAM and a flash memory, a hard disk, an optical disk, or the like. For example, the memory 141 stores projection data, reconstructed image data, and/or the like therein. The projection data and/or reconstructed image data may be stored in a server group (cloud) connected with the X-ray CT apparatus 100 through the network. For example, the memory 141 also stores therein a computer program to cause the circuit included in the X-ray CT apparatus 100 to achieve its function.

The display 142 displays various types of information. For example, the display 142 outputs a CT image generated with the processing circuitry 144, a GUI to receive various operations from the operator, and/or the like. For example, the display 142 is a liquid crystal display or a CRT display. The display 142 may be provided on the gantry 110. The display 142 may be of a desktop type, formed of a tablet terminal, or the like capable of performing wireless communications with the main member of the console 140.

The input interface 143 receives various input operations from the operator, converts the received input operations into electrical signals, and outputs the electrical signals to the processing circuitry 144. For example, the input interface 143 is achieved with a mouse, a keyboard, a trackball, a switch, a button, a joystick, a touch pad to perform an input operation by a touch on an operation surface thereof, a touch screen in which a display screen is united with a touch pad, a non-contact input circuit using an optical sensor, a sound input circuit, or the like. The input interface 143 may be formed of a tablet terminal or the like capable of performing wireless communications with the main member of the console 140. The input interface 143 is not limited to a structure including physical operation components, such as a mouse and a keyboard. For example, examples of the input interface 143 also include an electrical signal processing circuit receiving an electrical signal corresponding to an input operation from an external input device provided separately from the console 140, and outputting the electrical signal to the processing circuitry 144.

The processing circuitry 144 controls operations of the whole X-ray CT apparatus 100. For example, the processing circuitry 144 includes a acquisition function 144a, an output function 144b, and a control function 144c. The processing circuitry 144 is achieved with, for example, a processor.

For example, the processing circuitry 144 reads a computer program corresponding to the acquisition function 144a from the memory 141 and executes the computer program to acquire CT image data in which the blood vessel of the subject P is represented. The acquisition function 144a is an example of the acquirer.

For example, first, the acquisition function 144a controls the X-ray CT apparatus 100 to execute scan. The acquisition function 144a can execute scan of various methods, such as conventional scan, helical scan, and step-and-shoot technique.

Specifically, the acquisition function 144a controls the couch drive device 132 to move the subject P into an imaging port of the gantry 110. The acquisition function 144a also controls the X-ray high-voltage device 114 to supply high voltage to the X-ray tube ill, to irradiate X-rays to the subject P in a state in which a contrast medium is injected into the blood vessel thereof. The acquisition function 144a also regulates the aperture and the position of the collimator 117. The acquisition function 144a also controls the controller 115 to rotate the rotary unit including the rotary frame 113. The acquisition function 144a also causes the DAS 118 to acquire detection data. In the detection data acquired with the DAS 118, the blood vessel of the subject P is imaged with the contrast medium.

For example, the acquisition function 144a generates data obtained by subjecting the detection data output from the DAS 118 to preprocessing, such as logarithmic transformation, offset correction, sensitivity correction between channels, and beam hardening correction. The data (detection data) before being subjected to preprocessing and preprocessed data may be referred to as projection data as a general term.

The acquisition function 144a also generates CT image data in which the blood vessel of the subject P is represented from the projection data acquired using the contrast medium. For example, the acquisition function 144a subjects the preprocessed projection data to reconstruction using filtered back-projection and/or iterative approximation reconstruction to generate CT image data. For example, the acquisition function 144a also generates a plurality of pieces of tomographic image data from the preprocessed projection data, and converts the pieces of tomographic image data by a publicly known method to generate CT image data.

Examples of the reconstruction method include a full-scan method and a half-scan method. The full-scan method is a method of performing reconstruction using projection data for the whole circumference (360°) of the subject P. The half-scan method is a method of performing reconstruction using projection data for 180°+a fan angle. Either of the reconstruction methods is applicable to the present embodiment.

For example, the processing circuitry 144 reads a computer program corresponding to the output function 144b from the memory 141 and executes the computer program to store the generated CT image data in the memory 141 and transmit the CT image data to the image storage apparatus 20 and/or the medical information processing apparatus 30. The output function 144b also displays the CT image data on the display 142. For example, the output function 144b generates a display image, such as a volume rendering image, a curved multi planar reconstruction (CPR) image, a multi planar reconstruction (MPR) image, and a stretched multi planar reconstruction (SPR) image, on the basis of the CT image data, and displays the generated display image on the display 142. For example, the processing circuitry 144 reads a computer program corresponding to the control function 144c from the memory 141 and executes the computer program to control various functions of the processing circuitry 144 on the basis of the input operation received from the operator through the input interface 143.

In the X-ray CT apparatus 100 illustrated in FIG. 2, each of the processing functions is stored in the form of a computer program executable with a computer in the memory 141. The processing circuitry 144 is a processor reading a computer program from the memory 141 and executing the computer program to achieve the function corresponding to the computer program. In other words, the processing circuitry 144 in the state of reading each computer program has a function corresponding to the read computer program. FIG. 2 illustrates the case where the single processing circuit 144 achieves each of the processing functions of the acquisition function 144a, the output function 144b, and the control function 144c, but the embodiment is not limited thereto. For example, a plurality of independent processors may be combined to form the processing circuitry 144, and the functions may be achieved by executing the computer programs with the processors. The processing functions included in the processing circuitry 144 may properly be distributed or integrated into a single or a plurality of processing circuits.

FIG. 2 illustrates one X-ray tube 111 and one X-ray detector 112. Specifically, FIG. 2 illustrates the case where the X-ray CT apparatus 100 is of a single-tube type. However, the X-ray CT apparatus 100 may be a multi-tube X-ray CT apparatus, in which a plurality of pairs of the X-ray tube 111 and the X-ray detector 112 are mounted on the rotary frame 113.

FIG. 2 illustrates the case where the X-ray tube 111 and the X-ray detector 112 serve as one unitary piece and are rotated around the subject P. However, X-ray CT apparatuses have various types, such as a rotate/rotate type (third-generation CT) in which the X-ray tube and the X-ray detector rotate around the subject as one unitary piece, and a stationary/rotate-type (fourth-generation CT) in which a number of X-ray detection elements arrayed in a ring shape are fixed and only the X-ray tube rotates around the subject. Either of the types is applicable to the present embodiment.

FIG. 2 also illustrates the case where the X-ray tube 111 generates X-rays, but the embodiment is not limited thereto. For example, instead of the X-ray tube 111, X-rays may be generated using the fifth-generation method including a focus coil focusing the electron beam generated from the electron gun, a deflection coil electromagnetically deflecting the electron beam, and a target ring surrounding the half circumference of the subject and generating X-rays by collision of the deflected electron beam.

The console 140 may execute a plurality of functions with the single console, or a plurality of functions may be executed with separate consoles. For example, separate consoles may include the functions of the processing circuitry 144, such as the acquisition function 144a, the output function 144b, and the control function 144c, in a distributed manner. The processing circuitry 144 is not limited to the case of being included in the console 140, but may be included in an integrated server performing processing on detection data acquired with a plurality of medical image diagnostic apparatuses together.

The term "processor" used in the explanation described above means a circuit, such as a CPU, a graphics processing unit (GPU), an application specific integrated circuit (ASIC), and a programmable logic device (such as a simple programmable logic device (SPLD), a complex programmable logic device (CPLD), and a field programmable gate array (FPGA)). The processor reads and executes a computer program stored in the memory 33 or the memory 141 to achieve the function.

The processors in the present embodiment are not limited to the case where each processor is formed as a single circuit, but a plurality of independent circuits may be combined to be formed as a processor to achieve the function. FIG. 1 and FIG. 2 illustrate the case where the single memory 33 or the memory 141 stores the computer programs corresponding to the individual processing functions therein. However, a plurality of memories 33 may be arranged in a distributed manner, and the processing circuitry 34 may read corresponding computer programs from the individual memories 33. In the same manner, a plurality of memories 141 may be arranged in a distributed manner, and the processing circuitry 144 may read corresponding computer programs from the individual memories 141. As another example, instead of storing computer programs in the memory 33 and the memory 141, the computer programs may be directly incorporated in the circuit of the processor. In this case, the processor reads and executes the computer program incorporated in the circuit thereof to achieve the function.

An example of the structure of the medical information processing system 1 has been described above. With the structure, the medical information processing apparatus 30 in the medical information processing system 1 provides information indicating reliability of the fluid index. Specifically, by the processing performed with the processing circuitry 34 described in detail below, the medical information processing apparatus 30 specifies a deformed region in which the degree of meandering changes due to insertion of the device into the blood vessel, and outputs the specified deformed region in association with the fluid index, to provide information indicating reliability of the fluid index. The following is a detailed explanation of processing performed with the medical information processing apparatus 30 according to the first embodiment.

Figure 3:
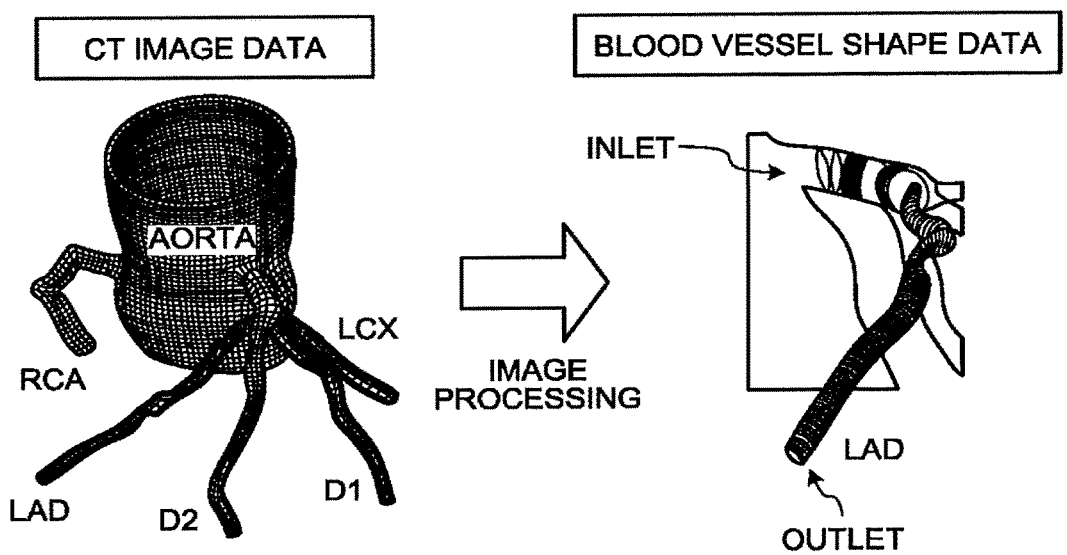
FIG. 3 is a diagram illustrating an example of CT image data according to the first embodiment.

First, the acquisition function 34a acquires CT image data representing the blood vessel of the subject P from the X-ray CT apparatus 100 or the image storage apparatus 20, and stores the CT image data in the memory 33. For example, the acquisition function 34a acquires CT image data illustrated in the left drawing of FIG. 3, and stores the CT image data in the memory 33. FIG. 3 is a diagram illustrating an example of CT image data according to the first embodiment. Specifically, the left drawing of FIG. 3 illustrates CT image data representing the aorta of the subject P and a plurality of blood vessels branching from the aorta. Specifically, the acquisition function 34a acquires CT image data representing the coronary artery of the subject P.

Thereafter, the specification function 34b extracts the blood vessel shape from the CT image data. In this operation, the specification function 34b may extract the blood vessel shape for all the blood vessels represented in the CT image data, or extract the blood vessel shape for part of the blood vessels represented in the CT image data. For example, in the case of extracting the blood vessel shape for part of the blood vessels represented in the CT image data, first, the specification function 34b sets the target region. As an example, the specification function 34b sets the part LAD illustrated in the left drawing of FIG. 3 as the target region by receiving an instruction from the operator through the input interface 31.

Thereafter, as illustrated in the right drawing of FIG. 3, the specification function 34b extracts the blood vessel shape of the target region LAD from the CT image data. For example, the specification function 34b extracts blood vessel shape data, such as the core line (coordinate information of the core line) of the blood vessel, the sections of the blood vessel and the lumen at the section perpendicular to the core line, the distance from the core line to the internal wall and the distance from the core line to the external wall in the cylindrical direction at a section perpendicular to the core line, as the blood vessel shape, by image processing on the CT image data.

Figure 4:
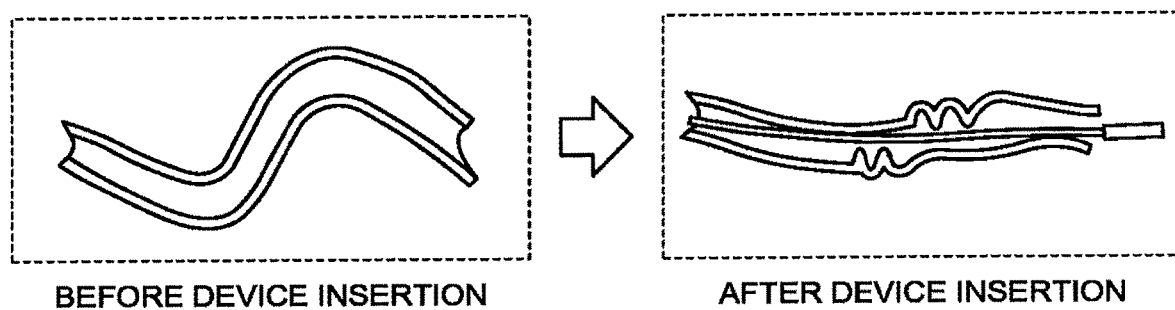
FIG. 4 is a diagram for explaining a deformed region according to the first embodiment.

Thereafter, the specification function 34b specifies the deformed region in which the degree of meandering changes due to insertion of the device into the blood vessel from the blood vessel shape data. The deformed region is a meandering region in the blood vessel of the subject P, as illustrated in the left drawing of FIG. 4. As illustrated in the right drawing of FIG. 4, when the device is inserted, the deformed region is deformed to reduce the meandering degree along the shape of the inserted device. FIG. 4 is a diagram for explaining the deformed region according to the first embodiment. FIG. 4 illustrates a region in which curves continue in a plurality of directions as the deformed region, but a region in which only a curve is generated may be included in the deformed region.

The device inserted into the blood vessel is, for example, a pressure wire, a stent placed in the blood vessel, a guide wire inserted into the blood vessel, a catheter, or the like. As an example, the following is an explanation of the case where the device inserted into the blood vessel is a pressure wire. The pressure wire is a device including a wire-shaped member and a pressure gauge. The pressure wire is inserted into the blood vessel, and thereafter measures the pressure and/or the fractional flow reserve (FFR) at each of positions in the blood vessel using the pressure gauge provided at the distal end portion thereof. FFR is a ratio of the pressure in the proximal portion in the blood vessel close to the aorta to the pressure in the distal portion distant from the aorta, and expressed with "FFR=Pd (pressure in the distal portion)/Pa (pressure in the proximal portion)".

For example, the specification function 34b acquires blood vessel structure information from the blood vessel shape data illustrated in the right drawing of FIG. 3, and specifies the deformed region on the basis of the acquired blood vessel structure information. The blood vessel structure information is, for example, the thickness of the blood vessel, the length of the blood vessel, the thickness of the blood vessel wall, the curvature of the blood vessel, the torsion of the blood vessel, the property of the blood vessel (such as calcification and plaque), the stiffness of the blood vessel, and the like.

As an example, the specification function 34b acquires the curvature and the torsion of the blood vessel, as the blood vessel structure information, from the blood vessel shape data illustrated in the right drawing of FIG. 3. Thereafter, the specification function 34b acquires the degree of meandering on the basis of the curvature and the torsion. Thereafter, on the basis of the degree of meandering, the specification function 34b determines whether the degree of meandering changes at each of positions of the blood vessel shape data when the pressure wire is inserted. For example, the specification function 34b determines whether the degree of meandering changes at each of positions of the blood vessel shape data, according to whether the quantity of change in curvature and torsion of the blood vessel before and after the insertion of the pressure wire exceeds the threshold. The specification function 34b specifies a set of positions at which it is determined that the degree of meandering changes, as the deformed region.

In addition to the degree of meandering, the specification function 34b may also use structure information of the pressure wire. For example, the specification function 34b acquires structure information of the pressure wire, and determines whether the degree of meandering changes at each of positions of the blood vessel shape data, on the basis of the degree of meandering and the structure information of the pressure wire. The structure information of the pressure wire is, for example, the thickness of the pressure wire, the length of the pressure wire, the stiffness of the pressure wire, the stress of the pressure wire, the operable range of the pressure wire, and the like. The structure information of the pressure wire is an example of structure information of the device.

As an example, the specification function 34b calculates the force (elastic force) received at each of positions of the blood vessel shape data from the pressure wire, on the basis of the degree of meandering acquired from the blood vessel shape data and the structure information of the pressure wire. The specification function 34b determines whether the degree of meandering changes at each of positions in the blood vessel shape, according to whether the elastic force exceeds the threshold. As another example, the specification function 34b converts the calculated elastic force into the quantities of change in the curvature and the torsion of the blood vessel, on the basis of a table or the like providing relation between the force applied onto the blood vessel and deformation. The specification function 34b determines whether the degree of meandering changes at each of positions in the blood vessel shape, according to whether the quantities of change exceed the threshold. The specification function 34b specifies a set of positions at which it is determined that the degree of meandering changes, as the deformed region.

The calculation function 34c calculates the fluid index in the blood vessel of the subject P. For example, the calculation function 34c executes fluid analysis on the basis of the blood vessel shape data extracted with the specification function 34b from the CT image data, to calculate the fluid index at each of positions in the blood vessel.

For example, first, the calculation function 34c sets analysis conditions for fluid analysis. Specifically, the calculation function 34c sets the physical values of the blood, conditions for iterative calculation, the initial value of analysis, and the like, as the analysis conditions. For example, the calculation function 34c sets the viscosity and the density of the blood, and the like, as the physical values of the blood. The calculation function 34c sets the maximum number of times of iteration, a mitigation coefficient, an allowable value for residuals, and the like for iterative calculation as the conditions for iterative calculation. The calculation function 34c also sets the initial values of the flow rate, the pressure, the fluid resistance, the pressure boundary, and the like, as the initial value of analysis. The various values used with the calculation function 34c may be incorporated in advance in the system, or interactively defined by the operator.

The calculation function 34c executes fluid analysis using the blood vessel shape data and the analysis conditions, to calculate the fluid index in the blood vessel. For example, the calculation function 34c calculates the fluid index, such as the pressure, the flow rate of the blood, the flow velocity of the blood, the vector, the shear stress, and the like, at each of positions in the blood vessel, on the basis of the blood vessel shape data, such as the contours of the lumen and the external wall of the blood vessel, the section of the blood vessel, and the core line, and the analysis conditions, such as the physical values of the blood, the conditions for iterative calculation, and the initial values of analysis. As an example, the calculation function 34c performs fluid analysis using the blood vessel shape data illustrated in the right drawing of FIG. 3 and the analysis conditions, to calculate the fluid index, such as the pressure, the flow rate of the blood, the flow velocity of the blood, the vector, and the shear stress, at each of predetermined positions along the core line from the boundary of the inlet to the boundary of the outlet of the target region LAD. Specifically, the calculation function 34c calculates distribution of the pressure, the flow rate of the blood, the flow velocity of the blood, the vector, the shear stress, and the like for the target region LAD.

For example, the calculation function 34c calculates the fluid index, on the basis of the pressure, the flow rate of the blood, the flow velocity of the blood, the vector, the shear stress, and the like calculated at each of positions in the blood vessel. As an example, the calculation function 34c calculates distribution of FFR in the target region LAD, on the basis of distribution of the pressure in the target region LAD.

Thereafter, the output function 34d outputs the deformed region in association with the fluid index calculated with the calculation function 34c. The following explanation illustrates the case where the deformed region is displayed on the display 32 in association with FFR, as an example.

Figure 5:
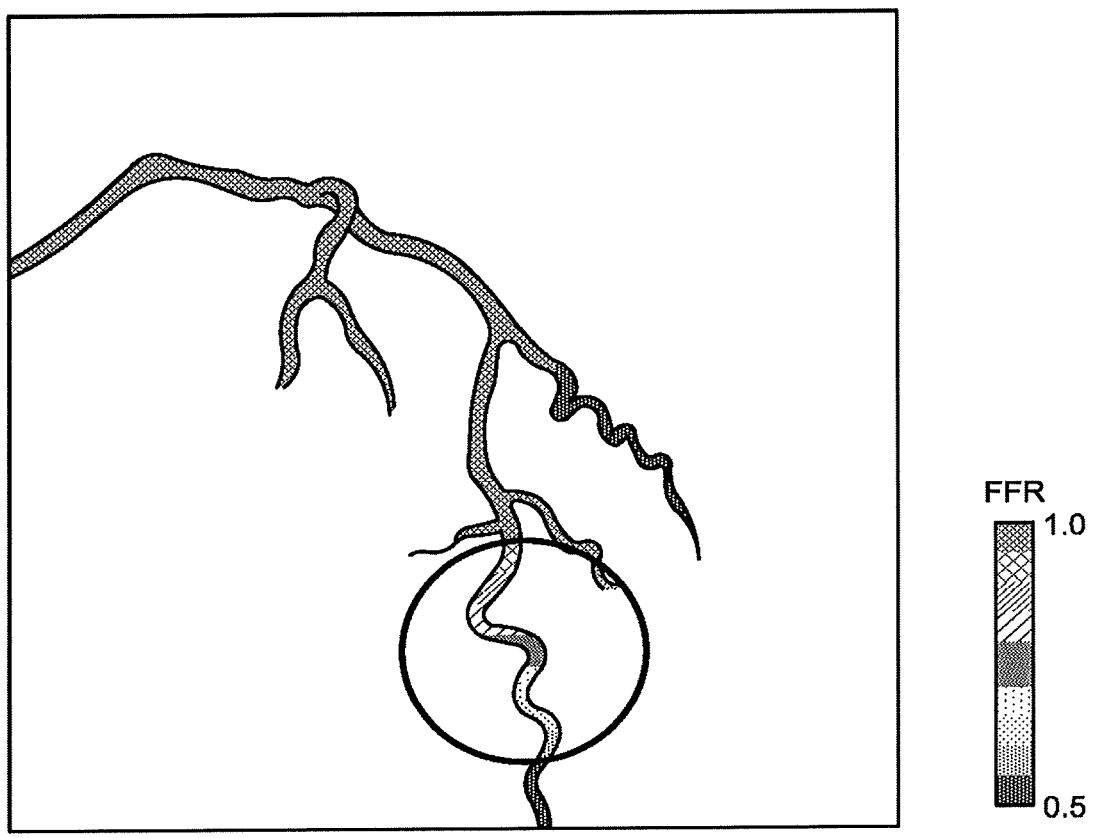
FIG. 5 is a diagram illustrating an example of display of a color image and the deformed region according to the first embodiment.

For example, first, the output function 34d generates image data illustrating distribution of FFR in the blood vessel of the subject P. As an example, the output function 34d reflects the values of the FFR on the CT image data illustrated in the left drawing of FIG. 3 in accordance with a color table, to generate a color image illustrated in FIG. 5. FIG. 5 is a diagram illustrating an example of display of the color image and the deformed region according to the first embodiment. FIG. 5 illustrates a color image of nine colors in which the color of the target region LAD in the CT image data is changed with each of reference values serving as boundaries. The reference values are values obtained by dividing the values from "0.5" to "1.0" into nine.

The output function 34d displays the color image and the deformed region in association with each other. For example, as illustrated in FIG. 5, the output function 34d displays the color image on the display 32, and displays a circle indicating the deformed region on the color image in a superimposed manner. As another example, the output function 34d displays the color image and a display image, such as a volume rendering image, on the display 32, and displays a circle indicating the deformed region on the display image in a superimposed manner.

In this state, the operator, such as a doctor, can judge the state of the blood flow of the subject P and/or make a treatment plan with reference to distribution of the FFR indicated with the color image. The operator can also recognize that the FFR in the deformed region indicated with the circle in FIG. 5 can be different from the FFR measured using the pressure wire.

Specifically, the FFR indicated with the color image in FIG. 5 is calculated on the basis of the CT image data, and indicates the FFR in the blood vessel in the state in which no pressure wire is inserted. By contrast, when the FFR is measured using the pressure wire, the blood vessel is deformed with the pressure wire inserted into the blood vessel, and the state of the blood flow is also changed, as illustrated in FIG. 4. The FFR indicated with the color image and the FFR measured using the pressure wire indicate the FFR before and after deformation of the blood vessel due to insertion of the pressure wire, respectively, and their values may deviate from each other.

In the following explanation, the FFR calculated on the basis of the CT image data is also referred to as CT-FFR. CT-FFR is an example of the fluid index in the blood vessel in the state in which the device is not inserted. In the following explanation, the FFR measured using the pressure wire is also referred to as Wire-FFR. Wire-FFR is an example of the fluid index in the blood vessel in the state in which the device is inserted.

After the pressure wire is inserted, the curvature of the meandering blood vessel decreases, and the blood vessel resistance value caused by the curved vessel decreases. For this reason, Wire-FFR is larger than CT-FFR at the same position in many cases. In other words, in a meandering blood vessel, CT-FFR exhibits a stricter result than that of Wire-FFR in many cases. When only CT-FFR is used, there is the possibility that a surgical operation is performed for a blood vessel that does not require treatment.

By contrast, the output function 34d displays the deformed region to notify the operator that the CT-FFR in the deformed region may be different from the Wire FFR. This structure enables the operator to make a treatment plan on the basis of the CT-FFR (CT-FFR highly correlated with Wire-FFR) in the region other than the deformed region, make a treatment plan on the basis of the CT-FFR of the deformed region in consideration of its difference from Wire-FFR, and/or additionally measure Wire-FFR.

FIG. 5 illustrates the case where a circle indicates the deformed region, but the embodiment is not limited thereto. For example, the output function 34d may indicate the deformed region with any figure, such as a rectangle and a bar. As another example, the output function 34d may indicate the deformed region with a color. As an example, the output function 34d displays a color image in which the CT-FFR in the deformed region is displayed with a predetermined color (such as black and white).

Figure 6:
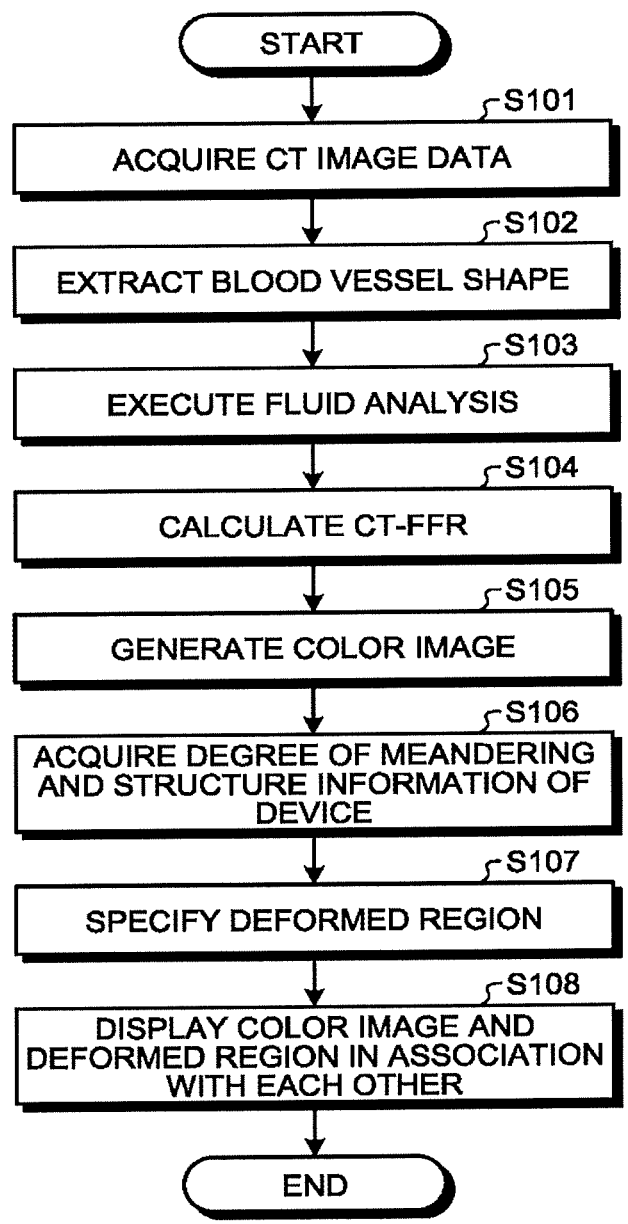
FIG. 6 is a flowchart for explaining a series of flows of a process of a medical information processing apparatus according to the first embodiment.

The following is an explanation of an example of a process performed with the medical information processing apparatus 30. FIG. 6 is a flowchart for explaining a flow of a series of processes performed with the medical information processing apparatus 30 according to the first embodiment. Step S101 is a step corresponding to the acquisition function 34a. Step S102, Step S106, and Step S107 are steps corresponding to the specification function 34b. Step S103 and Step S104 are steps corresponding to the calculation function 34c. Step S105 and Step S108 are steps corresponding to the output function 34d.

First, the processing circuitry 34 acquires CT image data representing the blood vessel of the subject P from the X-ray CT apparatus 100 or the image storage apparatus 20, and stores the CT image data in the memory 33 (Step S101). Thereafter, the processing circuitry 34 reads the CT image data from the memory 33, to extract the blood vessel shape from the CT image data (Step S102). Thereafter, the processing circuitry 34 executes fluid analysis using the extracted blood vessel shape (Step S103), to calculate the CT-FFR (Step S104). The processing circuitry 34 also generates a color image illustrating distribution of the calculated CT-FFR (Step S105).

The processing circuitry 34 also acquires the degree of meandering based on the blood vessel shape and structure information of the device (Step S106). Thereafter, the processing circuitry 34 specifies the deformed region on the basis of the degree of meandering and the structure information of the device (Step S107). The processing circuitry 34 displays the color image illustrating distribution of the CT-FFR in association with the deformed region (Step S108), and ends the processing.

Steps S103, S104, and S105 relating to generation of a color image and Steps S106 and S107 relating to specification of the deformed region may be performed in any order, and the steps may be performed in parallel.

As described above, according to the first embodiment, the acquisition function 34a acquires CT image data representing the blood vessel of the subject P. The specification function 34b extracts the blood vessel shape from the CT image data to determine the degree of meandering in each of regions from the extracted blood vessel shape and specify, on the basis of the degree of meandering, the deformed region in which the degree of meandering is changed due to insertion of the device into the blood vessel. The calculation function 34c calculates the fluid index in the blood vessel of the subject P. The output function 34d outputs the deformed region in association with the fluid index in the blood vessel of the subject P. With this structure, the medical information processing apparatus 30 according to the first embodiment can provide information indicating reliability of the fluid index.

The first embodiment described above illustrates the case of determining the degree of meandering on the basis of blood vessel structure information, such as the curvature and the torsion in the blood vessel shape. By contrast, the second embodiment illustrates the case of determining the degree of meandering on the basis of the fluid index.

The medical information processing apparatus 30 according to the second embodiment has a similar configuration to that of the medical information processing apparatus 30 according to the first embodiment illustrated in FIG. 1, and different from the medical information processing apparatus 30 according to the first embodiment in part of processing performed with the specification function 34b, the calculation function 34c, and the output function 34d. For this reason, points having the same structures as those explained in the first embodiment are denoted by the same reference numerals as those in FIG. 1, and an explanation thereof is omitted.

First, the acquisition function 34a acquires CT image data representing the blood vessel of the subject P, and the specification function 34b extracts the blood vessel shape from the CT image data. Thereafter, the calculation function 34c calculates the fluid index on the basis of the extracted blood vessel shape. The following is an explanation of the case where the calculation function 34c calculates CT-FFR as the fluid index. Thereafter, the specification function 34b determines the degree of meandering on the basis of the CT-FFR calculated with the calculation function 34c.

For example, the specification function 34b determines the degree of meandering on the basis of a change quantity between positions of the CT-FFR calculated with the calculation function 34c. Specifically, the specification function 34b determines the degree of meandering on the basis of a change quantity between positions of the fluid index in the blood vessel in the state in which the device is not inserted.

Figure 7:
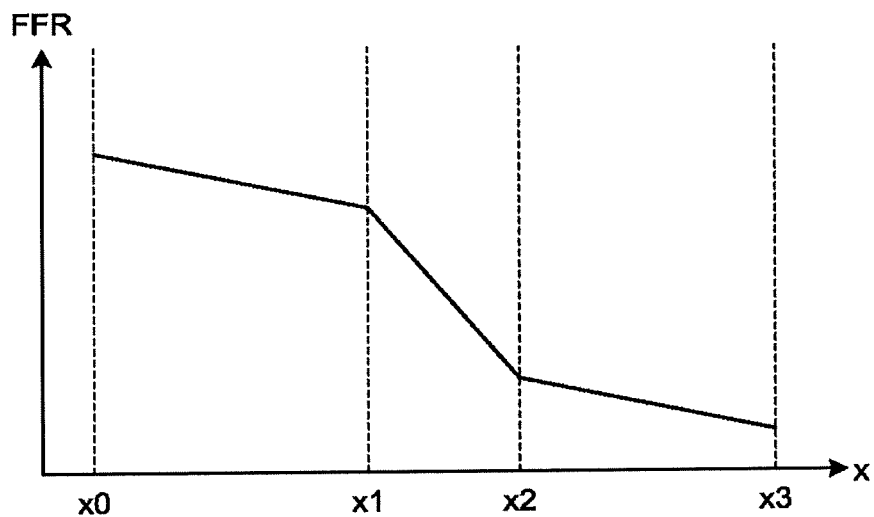
FIG. 7 is a diagram for explaining specification of the deformed region according to a second embodiment.

As an example, as illustrated in FIG. 7, the specification function 34b acquires CT-FFR at each of positions along the core line from the boundary of the inlet to the boundary of the outlet of the target region LAD in the blood vessel shape data. FIG. 7 is a diagram for explaining specification of the deformed region according to the second embodiment. In FIG. 7, the vertical axis indicates the value of FFR, and the horizontal axis indicates the position along the core line. For example, the position "x0" of the horizontal axis indicates the position of the inlet of the target region LAD. The position "x3" of the horizontal axis indicates the position of the outlet of the target region LAD.

In FIG. 7, the CT-FFR gently decreases in the region from the position "x0" to the position "x1", and in the region from the position "x2" to the position "x3". Specifically, the change quantity of the CT-FFR between positions is small in the region from the position "x0" to the position "x1", and in the region from the position "x2" to the position "x3". By contrast, the CT-FFR rapidly decreases in the region from the position "x1" to the position "x2". Specifically, the change quantity of the CT-FFR between positions is large in the region from the position "x1" to the position "x2".

The possible main cause of the large change quantity of the CT-FFR in the region from the position "x1" to the position "x2" is that, for example, the blood vessel in the region from the position "x1" to the position "x2" meanders and has a large blood vessel resistance value due to the curved vessel. Accordingly, the specification function 34b can determine the degree of meandering of each region such that the degree of meandering in the region from the position "x1" to the position "x2" increases. The specification function 34b specifies the deformed region on the basis of the degree of meandering. For example, on the basis of the degree of meandering, the specification function 34b determines whether the degree of meandering changes at each of positions of the blood vessel shape data when the pressure wire is inserted, and specifies a set of positions (for example, the region from the position "x1" to the position "x2") at which it is determined that the degree of meandering changes, as the deformed region.

The specification function 34b may specify the deformed region also using the blood vessel structure information. For example, the specification function 34b acquires the thickness of the blood vessel in the region from the position "x1" to the position "x2", and determines whether the main cause of the large change quantity of the CT-FFR between the positions is stenosis of the blood vessel. When the specification function 34b determines that the main cause of the large change quantity of the CT-FFR between the positions is not stenosis of the blood vessel, the specification function 34b determines the degree of meandering of each region such that the degree of meandering in the region from the position "x1" to the position "x2" increases, and specifies the deformed region on the basis of the degree of meandering.

As explained with reference to FIG. 7, the specification function 34b specifies the region from the position "x1" to the position "x2" as the deformed region. The output function 34d displays the deformed region on the display 32 in association with the color image or the like. This structure enables the output function 34d to notify the operator that the region from the position "x1" to the position "x2" is the deformed region and that the CT-FFR in the deformed region may be different from the Wire-FFR.

Figure 8:
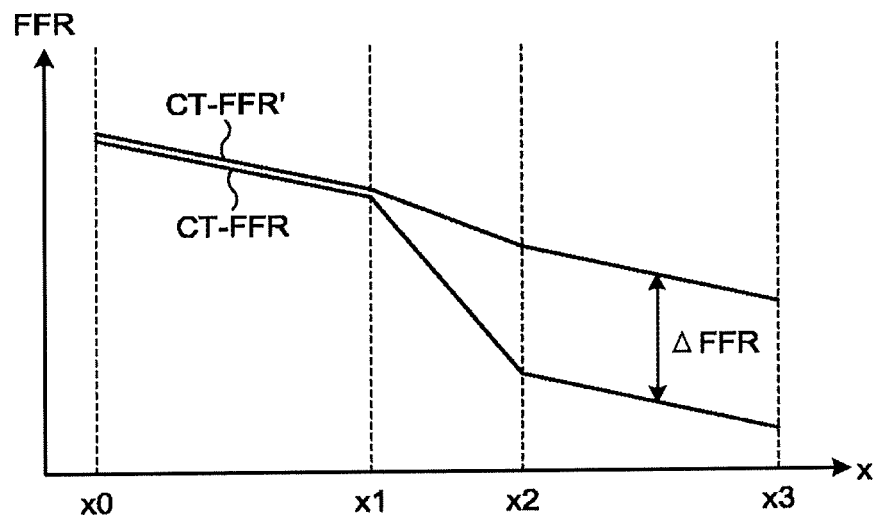
FIG. 8 is a diagram for explaining specification of the deformed region according to the second embodiment.

The following is an explanation of another example of specification of the deformed region with reference to FIG. 8. FIG. 8 is a diagram for explaining specification of the deformed region according to the second embodiment. In FIG. 8, the vertical axis indicates the value of FFR, and the horizontal axis indicates the position along the core line.

CT-FFR' illustrated in FIG. 8 indicates FFR obtained by estimating, with the calculation function 34c, deformation of the blood vessel shape occurring due to insertion of the pressure wire and performing calculation on the basis of the estimated deformed blood vessel shape. For example, the calculation function 34c deforms the blood vessel shape extracted from the CT image data such that the degree of meandering decreases (the curvature decreases) along the shape of the pressure wire, on the basis of the blood vessel structure information and the structure information of the pressure wire. Thereafter, the calculation function 34c calculates CT-FFR' on the basis of the deformed blood vessel shape. Specifically, CT-FFR' is an example of the fluid index in the blood vessel in the state in which the device is inserted. By contrast, the CT-FFR illustrated in FIG. 8 is an example of the fluid index in the blood vessel in the state in which the device is not inserted.

In FIG. 8, the CT-FFR and the CT-FFR' have substantially equal values in the region from the position "x0" close to the inlet of the target region LAD to the position "x1". Specifically, in the region from the position "x0" to the position "x1", a difference (hereinafter referred to as "ΔFFR") between the CT-FFR and the CT-FFR' has a small value. This means that it is estimated that the degree of meandering in the region from the position "x0" to the position "x1" is small and that the blood vessel shape is not deformed almost at all even when the pressure wire is inserted in calculation of the CT-FFR'.

By contrast, ΔFFR gradually increases in the region from the position "x1" to the position "x2". This means that it is estimated that the degree of meandering in the region from the position "x1" to the position "x2" is large and that the blood vessel shape will be deformed due to insertion of the pressure wire in calculation of the CT-FFR'. Accordingly, the specification function 34b can determine the degree of meandering in each of the regions such that the degree of meandering in the region from the position "x1" to the position "x2" increases. The specification function 34b specifies the deformed region on the basis of the degree of meandering. For example, on the basis of the degree of meandering, the specification function 34b determines whether the degree of meandering changes at each of positions of the blood vessel shape data when the pressure wire is inserted, and specifies a set of positions (for example, the region from the position "x1" to the position "x2") at which it is determined that the degree of meandering changes, as the deformed region.

ΔFFR has a large value in the region from the position "x2" to the position "x3". This is because ΔFFR occurring in the meandering region from the position "x1" to the position "x2" is left in the downstream, and does not necessarily indicate that the region from the position "x2" to the position "x3" meanders.

As explained with reference to FIG. 8, the specification function 34b specifies the region from the position "x1" to the position "x2" as the deformed region, in the region from the position "x0" to the position "x3". The output function 34d displays the deformed region on the display 32 in association with the color image or the like. For example, the output function 34d reflects the CT-FFR on the CT image data in accordance with the color table, to generate a color image illustrating distribution of the CT-FFR and display the generated color image and the deformed region in association with each other.

Figure 9:
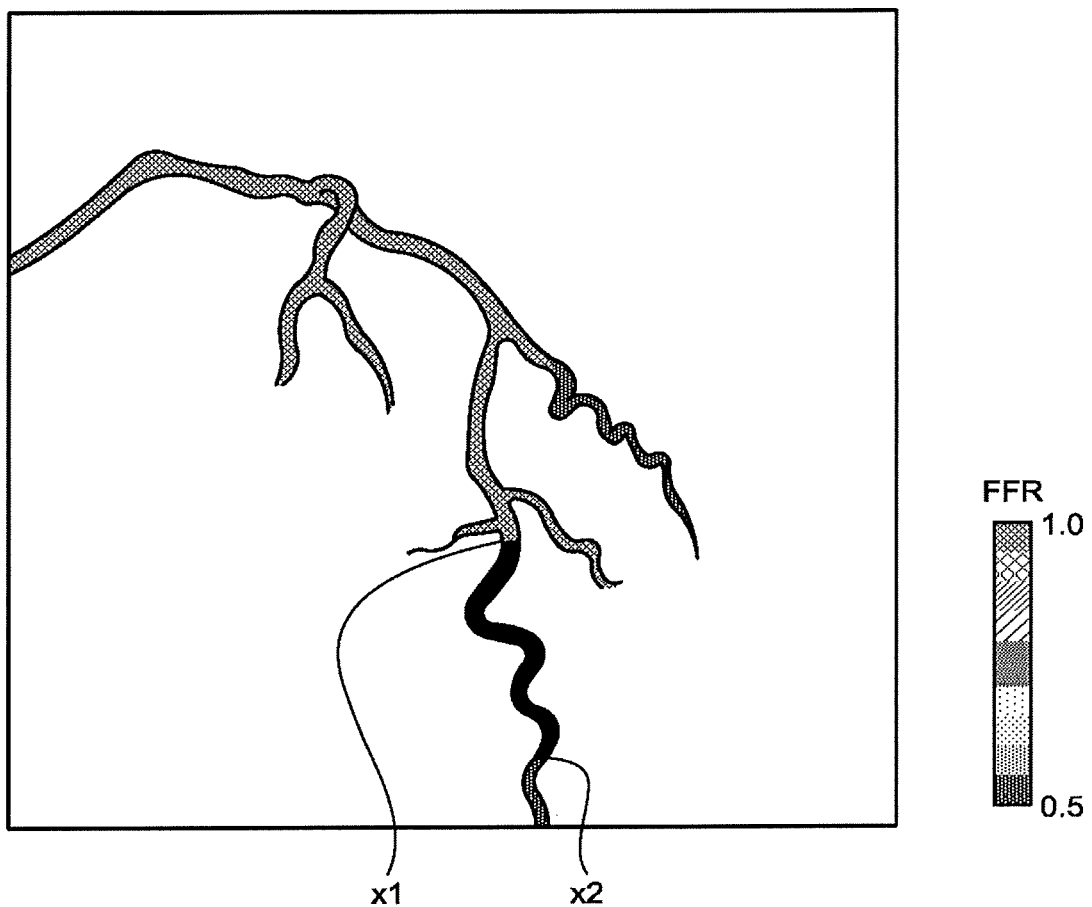
FIG. 9 is a diagram illustrating an example of display of the color image and the deformed region according to the second embodiment.

For example, the output function 34d displays a color image being a color image obtained by reflecting the values of the CT-FFR on the CT image data in accordance with the color table and in which the deformed region is displayed with a predetermined color. As an example, as illustrated in FIG. 9, the output function 34d displays a color image in which the region from the position "x1" to the position "x2" and specified as the deformed region is displayed in black. FIG. 9 is a diagram illustrating an example of display of the color image and the deformed region according to the second embodiment. In this state, the output function 34d may switch display of a color image with the deformed region displayed with a predetermined color to display of a color image in which the values of the CT-FFR is reflected on the deformed region, in response to reception of an instruction from the operator through the input interface 31.

In this manner, the output function 34d can notify the operator that the region from the position "x1 to the position "x2" is the deformed region and that the CT-FFR in the deformed region may be different from the Wire-FFR. This structure enables the operator to make a treatment plan on the basis of the CT-FFR (CT-FFR highly correlated with Wire-FFR) in the region other than the deformed region, make a treatment plan on the basis of the CT-FFR of the deformed region in consideration of its difference from Wire-FFR, and/or additionally measure Wire-FFR.

As another example, the output function 34d reflects the CT-FFR' on the CT image data in accordance with the color table, to generate a color image illustrating distribution of the CT-FFR' and display the generated color image and the deformed region in association with each other. Specifically, the output function 34d displays the deformed region in association with the fluid index in the blood vessel in the state in which the device is inserted. In this manner, the output function 34d can notify the operator that the region from the position "x1 to the position "x2" is the deformed region and that the CT-FFR' in the deformed region is different from the CT-FFR. This structure enables the operator to make a treatment plan on the basis of the CT-FFR' (CT-FFR' highly correlated with CT-FFR) in the region other than the deformed region, make a treatment plan on the basis of the CT-FFR' of the deformed region in consideration of its difference from CT-FFR, and/or additionally measure Wire-FFR.

Figure 10:
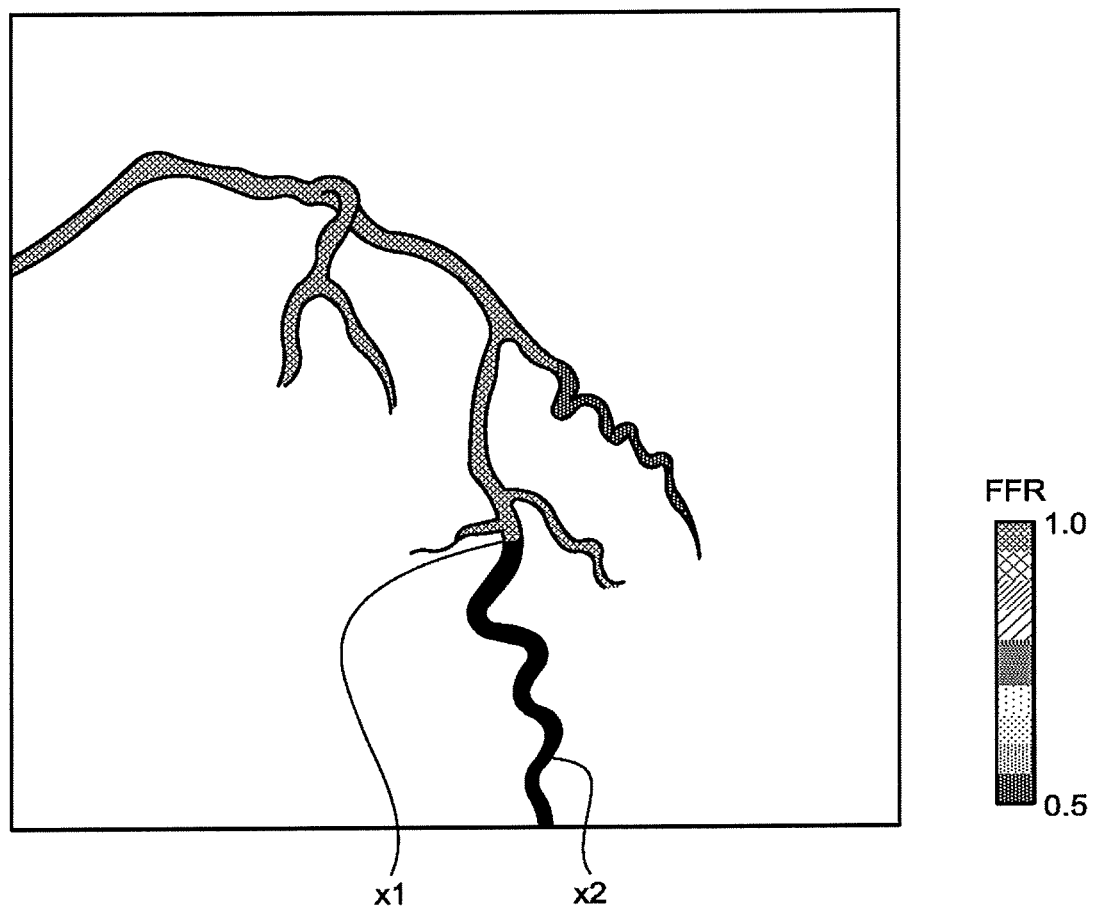
FIG. 10 is a diagram illustrating an example of display of the color image and the deformed region according to the second embodiment.

The region from the position "x2" to the position "x3" is similar to the deformed region in that the CT-FFR may deviate from the Wire-FFR, even when the region does not meander. Accordingly, the output function 34d may display the region from the position "x2" to the position "x3" in the same manner as the deformed region. For example, the specification function 34b specifies the region from the position "x1" to the position "x3" as the region in which the blood flow index changes, in the region from the position "x0" to the position "x3". Specifically, the specification function 34b specifies the downstream region of the position "x1" in the LAD as the region in which change in blood flow index occurs. As illustrated in FIG. 10, the output function 34d displays a color image in which the region (downstream region of the position "x1" in the LAD) from the position "x1" to the position "x3" is displayed in black. Specifically, the output function 34d outputs the region in which change in blood flow index occurs in the coronary artery. FIG. 10 is a diagram illustrating an example of display of the color image and the deformed region according to the second embodiment. In this case, the output function 34d can notify the operator that the CT-FFR in the region from the position "x1" to the position "x3" may be different from Wire FFR.

As another example, the output function 34d can notify the operator that the CT-FFR' in the region from the position "x1" to the position "x3" is different from the CT-FFR.

The downstream region of the position "x1" illustrated in FIG. 10 is a region in which change in blood flow index occurs due to the deformed region. However, the region in which change in blood flow index occurs may appear due to causes other than the deformed region. For example, when Wire-FFR is measured, even when the blood vessel shape is not changed, there are cases where the blood flow index changes due to inhibition of the blood flow with the pressure wire inserted into the blood vessel. As an example, due to insertion of the pressure wire into the blood vessel, the intravascular section is reduced by the section of the pressure wire. Due to influence of the pressure wire on the blood flow, a difference may occur between the CT-FFR and the Wire-FFR.

For this reason, the specification function 34b may specify the region in which change in blood flow index occurs, regardless of whether the change is caused by the deformed region. For example, the specification function 34b executes fluid simulation on the basis of the blood vessel structure information and the structure information of the pressure wire, to estimate the influence of the pressure wire on the blood flow in the blood vessel. As an example, the specification function 34b executes fluid simulation in the state in which no pressure wire is inserted into the blood vessel and fluid simulation in the state in which the pressure wire is inserted into the blood vessel, and specifies the region in which disagreement occurs between the two simulation results as the region in which change in blood flow index occurs. Thereafter, the output function 34d outputs the region in which change in blood flow index occurs.

Figure 11:
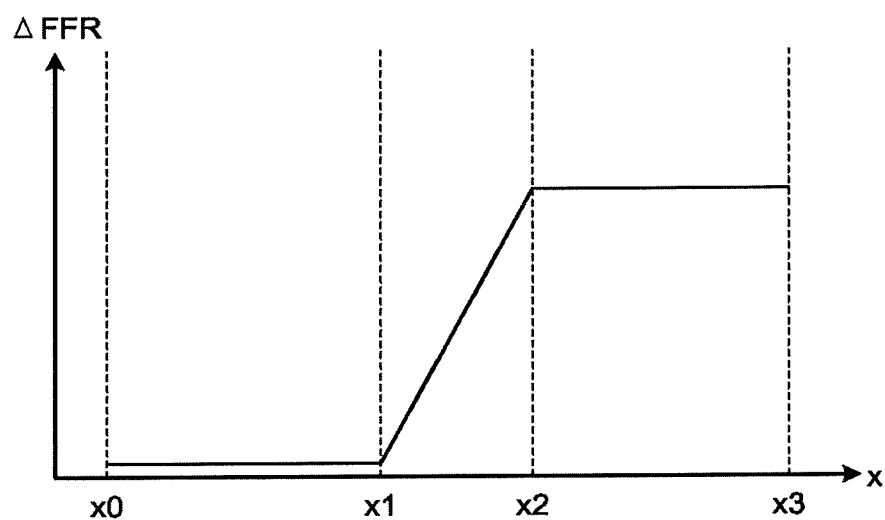
FIG. 11 is a diagram for explaining specification of the deformed region according to the second embodiment.

The following is an explanation of another example of specification of the deformed region with reference to FIG. 11. FIG. 11 is a diagram for explaining specification of the deformed region according to the second embodiment. The vertical axis in FIG. 11 illustrates ΔFFR serving as a difference between the CT-FFR and the C-FFR' illustrated in FIG. 8. In FIG. 11, the horizontal axis indicates the position along the core line.

In FIG. 11, ΔFFR is substantially fixed at a small value in the region from the position "x1" to the position "x1". Specifically, the change quantity of ΔFFR between positions is substantially 0 in the region from the position "x0" to the position "x1". This means that it is estimated that the degree of meandering in the region from the position "x0" to the position "x1" is small and that the blood vessel shape is not deformed almost at all even when the pressure wire is inserted in calculation of CT-FFR'.

By contrast, ΔFFR gradually increases in the region from the position "x1" to the position "x2". Specifically, the change quantity of ΔFFR between positions has a large value in the region from the position "x1" to the position "x2". This means that it is estimated that the degree of meandering in the region from the position "x1" to the position "x2" is large and that the blood vessel shape is deformed due to insertion of the pressure wire in calculation of CT-FFR'. Accordingly, the specification function 34b can determine the degree of meandering of each of the regions such that the degree of meandering in the region from the position "x1" to the position "x2" increases. Thereafter, the specification function 34b specifies the deformed region on the basis of the degree of meandering. For example, on the basis of the degree of meandering, the specification function 34b determines whether the degree of meandering changes in each of positions of the blood vessel shape data when the pressure wire is inserted, and specifies a set of positions (for example, the region from the position "x1" to the position "x2") for which it is determined that the degree of meandering changes, as the deformed region.

ΔFFR has a large value and is substantially fixed in the region from the position "x2" to the position "x3". Specifically, the change quantity of ΔFFR between positions is substantially 0 in the region from the position "x2" to the position "x3". This means that it is estimated that the degree of meandering in the region from the position "x2" to the position "x3" is small and that the blood vessel shape is not deformed almost at all even when the pressure wire is inserted in calculation of the CT-FFR'.

As explained with reference to FIG. 11, the specification function 34b specifies the region from the position "x1" to the position "x2" as the deformed region. The output function 34d displays the deformed region on the display 32 in association with the color image or the like. In this manner, the output function 34d can notify the operator that the region from the position "x1 to the position "x2" is the deformed region and that the CT-FFR in the deformed region may be different from the Wire-FFR. As another example, the output function 34d can notify the operator that the region from the position "x1 to the position "x2" is the deformed region and that the CT-FFR' in the deformed region is different from the CT-FFR.

The first and the second embodiments described above illustrate the case of displaying the deformed region in association with the fluid index calculated on the basis of the CT image data. By contrast, the third embodiment illustrates the case of displaying the deformed region in association with the fluid index measured using the pressure wire.

The medical information processing apparatus 30 according to the third embodiment has a similar configuration to that of the medical information processing apparatus 30 according to the first embodiment illustrated in FIG. 1, and different from the medical information processing apparatus 30 according to the first embodiment in part of processing performed with the output function 34d.

The medical information processing system 1 according to the third embodiment includes an X-ray diagnostic apparatus 200, instead of the X-ray CT apparatus 100, or in addition to the X-ray CT apparatus 100. The X-ray diagnostic apparatus 200 is an example of the medical image diagnostic apparatus 10. The points having the same structures as those explained in the first embodiment are denoted by the same reference numerals as those in FIG. 1, and an explanation thereof is omitted.

For example, the X-ray diagnostic apparatus 200 executes rotary imaging on the subject P injected with a contrast medium, and reconstruct three-dimensional X-ray image data (volume data) from projection data acquired with the rotary imaging. The three-dimensional X-ray image data is an example of medical image data representing the blood vessel of the subject P. The X-ray diagnostic apparatus 200 transmits the three-dimensional X-ray image data to the image storage apparatus 20 and the medical information processing apparatus 30.

Thereafter, the acquisition function 34a acquires the three-dimensional X-ray image data from the X-ray diagnostic apparatus 200 or the image storage apparatus 20. The specification function 34b extracts the blood vessel shape from the three-dimensional X-ray image data, to specify the deformed region from the extracted blood vessel shape. For example, the specification function 34b acquires the degree of meandering on the basis of the blood vessel structure information, such as the curvature and the torsion in the blood vessel shape, to specify the deformed region on the basis of the degree of meandering.

The X-ray diagnostic apparatus 200 also assists measurement of the fluid index. For example, when the operator is inserting a pressure wire into the blood vessel of the subject P, the X-ray diagnostic apparatus 200 sequentially acquires pieces of X-ray image data including the pressure wire, and successively displays the acquired pieces of X-ray image data. The X-ray images successively displayed in parallel with acquisition are also referred to as "fluoroscopic image". The operator can operate the pressure wire in the blood vessel of the subject P with reference to the fluoroscopic image and measure the pressure, the Wire-FFR, and the like at a desired position. The order of acquisition of three-dimensional X-ray image data, specification of the deformed region, and measurement of the fluid index may be any order. The following explanation illustrates the case where Wire-FFR is measured as the fluid index.

Thereafter, the output function 34d acquires the measured Wire-FFR. For example, the output function 34d acquires Wire-FFRs measured at a plurality of positions of the blood vessel of the subject P and positional information indicating the positions at which the individual Wire-FFRs have been measured. As an example, the output function 34d acquires a plurality of Wire-FFRs measured at individual predetermined positions from the boundary of the inlet to the boundary of the outlet of the LAD of the subject P and positional information indicating the positions at which the individual Wire-FFRs have been measured.

The positional information indicating the position in which the Wire-FFR has been measured is, for example, a distance from the landmark (such as the inlet or the branch point of the blood vessel) in the blood vessel. For example, first, the pressure wire including a distal end provided with a pressure gauge is inserted into the blood vessel of the subject P, and the pressure "P0" is measured in a state in which the distal end of the pressure wire is located at the inlet of the LAD. The following explanation is made on the assumption that the Wire-FFR in the inlet of the LAD is "1". In this case, for example, the output function 34d acquires the distance "0" from the inlet of the LAD, as the positional information indicating the position in which the Wire-FFR "1" has been measured.

Thereafter, the pressure "P1" is measured in a state in which the distal end of the pressure wire is located at a position with a distance "L1" from the inlet of the LAD. The distance "L1" corresponds to the length by which the pressure wire is further inserted after the pressure "P0" is measured. In this case, for example, the output function 34d acquires the distance "L1" from the inlet of the LAD, as the positional information indicating the position at which the Wire-FFR "P1/P0" has been measured. In the same manner, the output function 34d acquires the distance from the inlet of the LAD, as the positional information, for each of the Wire-FFRs measured for the individual positions in the LAD.

Thereafter, the output function 34d positions the acquired positional information with the three-dimensional X-ray image data. For example, first, the output function 34d specifies the position of the inlet of the LAD in the blood vessel shape extracted from the three-dimensional X-ray image data. Thereafter, the output function 34d specifies the position indicated with the positional information in the blood vessel shape, by regulating the distance from the specified position along the core line to be equal to the distance from the inlet of the LAD acquired as the positional information. In this manner, the output function 34d can specify the position at which the Wire-FFR has been measured in the blood vessel shape extracted from the three-dimensional X-ray image data and associate the position with the deformed region.

Thereafter, the output function 34d displays the deformed region on the display 32 in association with the Wire-FFR. For example, the output function 34d generates a graph having a vertical axis indicating the Wire-FFR measured at each of the positions of the LAD, and a horizontal axis indicating the position (such as the distance from the inlet of the LAD) at which the Wire-FFR has been measured, to display the deformed region in association with the horizontal axis of the generated graph. For example, the output function 34d generates a color image by reflecting the values of the Wire-FFR on the three-dimensional X-ray image data in accordance with the color table, to display a figure or the like indicating the deformed region on the color image. As another example, the output function 34d generates an X-ray image for display from the three-dimensional image data, to display the generated X-ray image and display the values of the Wire-FFR and a figure or the like indicating the deformed region on the X-ray image.

The Wire-FFR is smaller than the CT-FFR at the same position in many cases. In other words, in a meandering blood vessel, Wire-FFR often indicates a more optimistic result than that of CT-FFR. When only Wire-FFR is used, there is the possibility that no surgical operation is performed on the blood vessel requiring treatment. By contrast, the output function 34d displays the deformed region to notify the operator that the Wire-FFR in the deformed region may be different from the CT-FFR. The operator can make a treatment plan on the basis of the Wire-FFR (Wire-FFR highly correlated with CT-FFR) in the region other than the deformed region, make a treatment plan on the basis of the Wire-FFR of the deformed region in consideration of its difference from CT-FFR, and/or additionally perform CT scan or measure CT-FFR.

The first to the third embodiment have been described above, but embodiments may be performed in various different forms other than the embodiments described above.

The embodiments described above illustrate the case of specifying the deformed region on the basis of the blood vessel structure information or the fluid index. However, the embodiments are not limited thereto. For example, the specification function 34b may specify the deformed region by machine learning.

For example, the specification function 34b acquires a number of combinations of the blood vessel shape extracted from the CT image data, the CT-FFR, and the Wire-FFR, as training data. Thereafter, the specification function 34b specifies the deformed region from the blood vessel shape, in accordance with whether a difference (deviation) between the CT-FFR and the Wire-FFR is larger than the threshold. Thereafter, the specification function 34b learns the degree of deformation at each of each position in the deformed region and each position in the regions other than the deformed region in the blood vessel shape. The specification function 34b determines whether the degree of deformation of each region in the blood vessel shape newly extracted from the CT image data corresponds to the deformed region on the basis of the learning results, to specify the deformed region.

As another example, the specification function 34b acquires a number of combinations of CT image data I1 acquired in the state in which no pressure wire is inserted and CT image data 12 acquired in the state in which the pressure wire is inserted. Thereafter, the specification function 34b acquires a number of combinations of a blood vessel shape B1 extracted from the CT image data I1 and a blood vessel shape B2 extracted from the CT image data 12, as training data. Thereafter, using these pieces of training data, the specification function 34b learns change of the blood vessel shape occurring on the CT image data I1 due to insertion of the pressure wire. For example, the specification function 34b executes machine learning to generate a trained model M1 provided with a function to estimate the blood vessel shape B2 of the CT image data 12 acquired in the state in which the pressure wire is inserted, in response to reception of the blood vessel shape B1 extracted from the CT image data I1.

The trained model M1 is formed with, for example, a neural network. The neural network is a network having a structure in which adjacent layers arranged in a layered manner are combined and information is transmitted from the input layer side to the output layer side. For example, the specification function 34b inputs the blood vessel shape B1 as the input-side data to the neural network. In the neural network, information is transmitted in one direction from the input layer side to the output layer side while the layers are combined only between adjacent layers. The neural network outputs a blood vessel shape B1' obtained by changing the blood vessel shape B1.

For example, the specification function 34b executes deep learning for a multi-layer neural network using a plurality of pieces of training data, to generate the trained model M1. The multi-layer neural network is formed of, for example, an input layer, a plurality of intermediate layers (hidden layers), and an output layer.

For example, the specification function 34b regulates parameters of the neural network such that the neural network can output a preferable result when the blood vessel shape B1 is input. For example, the specification function 34b regulates the parameters of the neural network using a function (error function) indicating proximity of the blood vessel shape B1' output from the neural network when the blood vessel shape B1 is input to the output-side data (blood vessel shape B2). As an example, the specification function 34b repeatedly calculates the error function while the parameters are changed, to regulate the parameters such that the error function is minimized. Specifically, the specification function 34b causes the neural network to learn to minimize the error function. In this manner, the specification function 34b can generate the trained model M1 provided with a function to estimate the blood vessel shape B2 in response to input of the blood vessel shape B1.

After the trained model M1 is generated, when CT image data I1 is newly acquired, the specification function 34b extracts the blood vessel shape B1 from the CT image data I1, and inputs the extracted blood vessel shape B1 to the trained model M1. In this manner, the specification function 34b can acquire the blood vessel shape B1' serving as estimation of the blood vessel shape B2 of CT-image data 12 to be acquired in the state in which the pressure wire is inserted. The specification function 34b can specify the region in which disagreement occurs between the blood vessel shape B1 and the blood vessel shape B1', as the deformed region in which change of the blood vessel shape occurs due to insertion of the pressure wire.

As another example, the specification function 34b acquires a number of combinations of the blood vessel shape B1 extracted from the CT image data I1 and the deformed region specified on the Ct image data I1, as the training data. As an example, the specification function 34b acquires a labeled blood vessel shape B3 in which the deformed region is labeled for the blood vessel shape B1, as the deformed region specified on the CT image data I1. The labeled blood vessel shape B3 may be automatically generated with the specification function 34b, or manually prepared by the operator.

Using these pieces of training data, the specification function 34b learns change of the blood vessel shape occurring on the CT image data I1 due to insertion of the pressure wire. For example, the specification function 34b executes machine learning to generate a trained model M2 provided with a function to estimate the deformed region in response to input of the blood vessel shape B1 extracted from the CT image data I1.

The trained model M2 may be formed with, for example, a neural network. For example, the specification function 34b regulates the parameters of the neural network using an error function indicating proximity of the deformed region output from the neural network when the blood vessel shape B1 is input to the deformed region indicated with the output-side data (labeled blood vessel shape B3). In this manner, the specification function 34b can generate the trained model M2 provided with a function to estimate the deformed region in response to input of the blood vessel shape B1.

After the trained model M2 is generated, when CT image data I1 is newly acquired, the specification function 34b extracts the blood vessel shape B1 from the CT image data I1, and inputs the extracted blood vessel shape B1 to the trained model M2. In this manner, the specification function 34b can specify the deformed region in which change of the blood vessel shape occurs due to insertion of the pressure wire.

When the explanation described above illustrates the case of specifying the deformed region by machine learning, but the embodiments are not limited thereto. For example, the specification function 34b may specify the region in which change of the fluid index occurs due to insertion of the pressure wire, by machine learning.

For example, the specification function 34b acquires the blood vessel shape B1 extracted from the CT image data I1 and the structure information of the pressure wire, as the input-side data. The specification function 34b also acquires the region specified on the CT image data I1 and in which change of the fluid index occurs, as the output-side data.

Thereafter, the specification function 34b executes machine learning using a plurality of pieces of training data formed of combinations of the input-side data and the output-side data, to generate a trained model M3 provided with a function to estimate the region in which change of the fluid index occurs in response to input of the blood vessel shape B1.

After the trained model M3 is generated, when CT image data I1 is newly acquired, the specification function 34b extracts the blood vessel shape B1 from the CT image data I1, and inputs the extracted blood vessel shape B1 to the trained model M3. In this manner, the specification function 34b can specify the region in which change of the fluid index occurs due to insertion of the pressure wire.

The embodiments described above illustrate the case where the output function 34d displays the deformed region on the display 32. However, the embodiments are not limited thereto. For example, the output function 34d may output the deformed region specified with the specification function 34b to an external device connected with the medical information processing apparatus 30 through the network. In this case, the external device can display the deformed region output with the output function 34d on a display included in the external device. Specifically, the medical information processing apparatus 30 can provide the operator of the external device with information indicating reliability of the fluid index.

The embodiments described above illustrate the case where the calculation function 34c calculates the fluid index. However, the embodiments are not limited thereto. For example, the output function 34d may acquire the fluid index calculated in an external device through the network, and output the deformed region in association with the acquired fluid index. In this case, the processing circuitry 34 may include no calculation function 34c.

The embodiments described above illustrate the case where the output function 34d outputs the deformed region in association with the fluid index, but the embodiments are not limited thereto. Specifically, the output function 34d may output the deformed region without association with the fluid index. In this case, the processing circuitry 34 may include no calculation function 34c.

For example, the output function 34d generates a display image, such as a volume rendering image, on the basis of the CT image data, to display the generated display image on the display 32 and display a figure or the like indicating the deformed region on the display image. In this case, the medical information processing apparatus 30 can notify the operator that the fluid index (such as Wire-FFR) in the blood vessel in the state in which the device is inserted may be different from the fluid index (such as CT-FFR) in the blood vessel in which the device is not inserted, in the deformed region. The operator can make judgement, such as using both Wire-FFR and CT-FFR and reducing the weight of the fluid index, in making a treatment plan.

The embodiments described above illustrate the pressure wire as an example of the device inserted into the blood vessel, but the embodiments are not limited thereto. For example, the specification function 34b may specify the deformed region in which deformation occurs due to insertion of a stent into the blood vessel. In this case, the medical information processing apparatus 30 can notify the operator that the fluid index (fluid index before placement of the stent) in the blood vessel in the state in which the device is not inserted may be different from the fluid index (fluid index after placement of the stent) in the blood vessel in the state in which the device is inserted, in the deformed region.

For example, first the medical image diagnostic apparatus 10 acquires medical image data from the subject P before the stent is placed therein. Thereafter, the specification function 34b extracts the blood vessel shape from the medical image data, and specifies the deformed region from the extracted blood vessel shape. The calculation function 34c executes fluid analysis on the basis of the blood vessel shape, to calculate the fluid index in the blood vessel of the subject P. Thereafter, the output function 34d displays the deformed region on the display 32 in association with the fluid index.

In this state, the operator can make a treatment plan including stent placement, on the basis of the fluid index before placement of the stent. The operator can also recognize that the fluid index before placement of the stent may be different from the fluid index after placement of the stent, in the deformed region. For example, when the fluid index before placement of the stent indicates a strict result in the deformed region, the operator can recognize that the fluid index after placement of the stent does not always indicate a similar result, also in consideration of the possibility that additional treatment is required in addition to the stent placement. For this reason, the medical image diagnostic apparatus 10 acquires medical image data again after stent placement, and the calculation function 34c calculates the fluid index again. Thereafter, the operator can make a treatment plan, such as necessity of additional treatment, on the basis of the fluid index after stent placement.

The embodiments described above illustrate the case where the processing circuitry 34 in the medical information processing apparatus 30 includes the acquisition function 34a, the specification function 34b, the calculation function 34c, and the output function 34d. However, the embodiments are not limited thereto. For example, the processing circuit in the medical image diagnostic apparatus 10 may include functions corresponding to the acquisition function 34a, the specification function 34b, the calculation function 34c, and the output function 34d.

Figure 12:
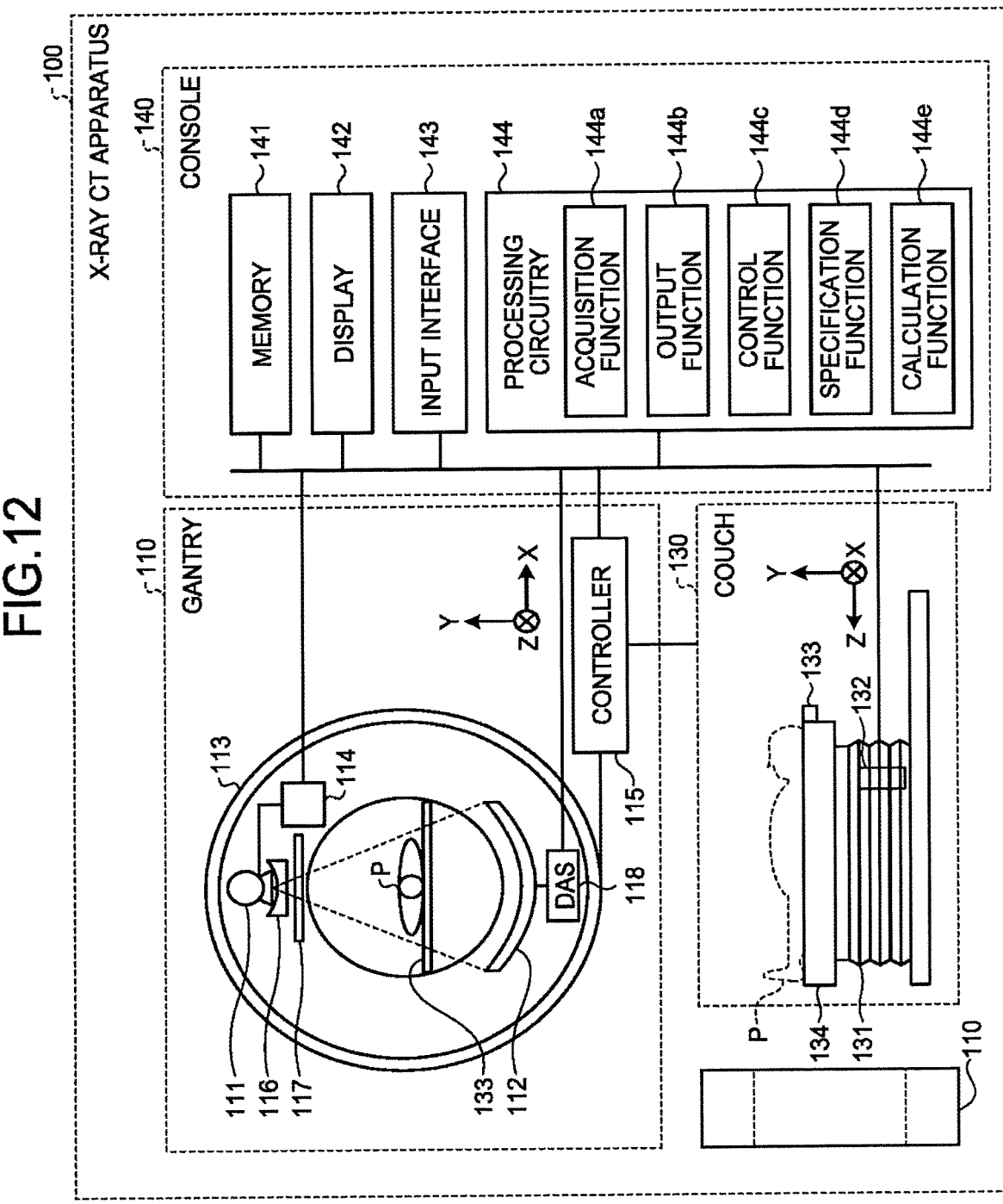
FIG. 12 is a block diagram illustrating an example of configuration of the X-ray CT apparatus according to a fourth embodiment.

For example, as illustrated in FIG. 12, the processing circuitry 144 in the X-ray CT apparatus 100 further includes a specification function 144d corresponding to the specification function 34b, and a calculation function 144e corresponding to the calculation function 34c. FIG. 12 is a block diagram illustrating an example of configuration of the X-ray CT apparatus 100 according to a fourth embodiment.

In the case illustrated in FIG. 12, first, the acquisition function 144a acquires CT image data representing the blood vessel of the subject P. Thereafter, the specification function 144d extracts the blood vessel shape from the CT image data, and specifies the deformed region from the extracted blood vessel shape. The calculation function 144e calculates the fluid index in the blood vessel of the subject P. Thereafter, the output function 144b outputs the deformed region in association with the fluid index. For example, the output function 144b associates image data indicating distribution of the fluid index in the blood vessel of the subject P with the deformed region, and displays them on the display 142. The output function 144b may acquire fluid index calculated in the external device, and output the deformed region in association with the acquired fluid index. The output function 144b may also output the deformed region without association with the fluid index. In this case, the processing circuitry 144 may include no calculation function 144e.

The processing circuitry 34 and/or the processing circuitry 144 may achieve the functions using a processor of an external device connected through the network. For example, the processing circuitry 34 reads and executes computer programs corresponding to the individual functions from the memory 33 and uses the server group (cloud) connected with the medical information processing apparatus 30 through the network as calculation resource, to achieve the acquisition function 34a, the specification function 34b, the calculation function 34c, and the output function 34d. As an example, the processing circuitry 34 achieves the specification function 34b by executing processing of extracting the blood vessel shape from the medical image data and/or processing of specifying the deformed region from the blood vessel shape on the cloud.

Constituent elements of the apparatuses according to the embodiments described above are functional and conceptual elements, and are not always physically configured as illustrated. Specifically, the specific forms of distribution and integration of the apparatuses are not limited to those illustrated, but all or part of them may be functionally or physically distributed or integrated in a desired unit in accordance with various loads and/or states of use. The whole or part of each of the processing functions executed in the apparatuses may be achieved with a CPU and a computer program analyzed and executed in the CPU, or as hardware by a wired logic.

The processing methods explained in the embodiments described above may be achieved by execution of a computer program prepared in advance with a computer, such as a personal computer and a work station. The computer program may be distributed through a network, such as the Internet.

The computer program may be recorded on a recording medium readable with a computer, such as a hard disk, a flexible disk (FD), a CD-ROM, an MO, and a DVD, and executed by being read from the recording medium with a computer.

At least one of the embodiments explained above enables provision of information indicating reliability of the fluid index.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
    processing circuitry configured to
        acquire medical image data representing a coronary artery of a subject;
        extract a blood vessel shape from the medical image data, and determine a region where changes in a Fractional-Flow-Reserve are estimated before and after a deformation of the coronary artery due to insertion of a pressure wire for measuring a Wire-Fractional-Flow-Reserve into the coronary artery, based on the extracted blood vessel shape;
        detect a position of the pressure wire in the coronary artery based on the acquired medical image data, and associate the Wire-Fractional-Flow-Reserve measured by the pressure wire with the position of the pressure wire where the Wire-Fractional-Flow-Reserve was measured; and
        identifiably display a particular position corresponding to the region in a distribution of the Wire-Fractional-Flow-Reserve by associating the region with the Wire-Fractional-How-Reserve associated with the position of the pressure wire.

2. The medical information processing apparatus according to claim 1, wherein
    the processing circuitry is further configured to determine a degree of meandering in each of regions from the extracted blood vessel shape, and determine, as the region, a region in which the degree of meandering decreases due to insertion of the pressure wire.

3. The medical information processing apparatus according to claim 1, wherein the processing circuitry is further configured to display the region in association with the distribution of the Wire-Fractional-Flow-Reserve in the coronary artery.

4. The medical information processing apparatus according to claim 3, wherein the processing circuitry is further configured to display the region in association with a distribution of the Fractional-Flow-Reserve in the coronary artery in a state in which the pressure wire is not inserted.

5. The medical information processing apparatus according to claim 3, wherein the processing circuitry is further configured to display the blood vessel image indicating the distribution of the Wire-Fractional-Flow-Reserve in the coronary artery and the region in association with each other.

6. The medical information processing apparatus according to claim 1, wherein the processing circuitry is further configured to determine a degree of meandering based on at least curvature and torsion of the blood vessel shape, and determine the region based on the acquired degree of meandering.

7. The medical information processing apparatus according to claim 6, wherein the processing circuitry is further configured to determine the region based on structure information of the pressure wire, in addition to the degree of meandering.

8. The medical information processing apparatus according to claim 7, wherein
the processing circuitry is further configured to determine the region based on information including at least one of thickness and stiffness of the pressure wire as the structure information.

9. The medical information processing apparatus according to claim 1, wherein the processing circuitry is further configured to determine the degree of meandering based on a change quantity between positions of the Fractional-Flow-Reserve in the coronary artery in a state in which the pressure wire is not inserted, and determine the region based on the determined degree of meandering.

10. The medical information processing apparatus according to claim 1, wherein the processing circuitry is further configured to estimate deformation of the blood vessel shape caused by insertion of the pressure wire, and calculate the Fractional-Flow-Reserve in the coronary artery in a state in which the pressure wire is inserted, based on the estimated deformed blood vessel shape.

11. The medical information processing apparatus according to claim 10, wherein the processing circuitry is further configured to determine a degree of meandering based on a difference between the Fractional-Flow-Reserve in the coronary artery in the state in which the pressure wire is inserted and the Fractional-Flow-Reserve in the coronary artery in a state in which the pressure wire is not inserted, and determine the region based on the determined degree of meandering.

12. The medical information processing apparatus according to claim 10, wherein the processing circuitry is further configured to determine a degree of meandering based on a change quantity, between positions, of a difference between the Fractional-Flow-Reserve in the coronary artery in the state in which the pressure wire is inserted in the coronary artery and in a state in which the pressure wire is not inserted, and determine the region based on the determined degree of meandering.

13. The medical information processing apparatus according to claim 1, wherein the processing circuitry is further configured to display a color map indicating the distribution of the Fractional-Flow-Reserve in the coronary artery, and display a low region in which a reliability of the Fractional-Flow-Reserve is lower with respect to other regions in the color map.

14. The medical information processing apparatus according to claim 13, wherein the processing circuitry is further configured to display the low region as a marker on the color map.

15. The medical information processing apparatus according to claim 1, wherein the processing circuitry is further configured to display information indicating that the Wire-Fractional-Flow-Reserve measured by the pressure wire is lower than a Simulated-Fractional-Flow-Reserve acquired by fluid analysis, as a reliability of the Fractional-Flow-Reserve.

16. A medical information processing apparatus, comprising:
processing circuitry configured to
acquire medical image data representing a coronary artery of a subject;
extract a blood vessel shape from the medical image data, and determine a region where changes in a Fractional-Flow-Reserve are estimated before and after a deformation of the coronary artery due to insertion of a pressure wire, based on the extracted blood vessel shape;
detect a position of the pressure wire in the coronary artery based on the acquired medical image data, and associate a Wire-Fractional-Flow-Reserve measured by the pressure wire with the position of the pressure wire where the Wire-Fractional-Flow-Reserve was measured; and
identifiably display a particular position corresponding to the region in a distribution of the Wire-Fractional-Flow-Reserve by associating the region with the Wire-Fractional-Flow-Reserve associated with the position of the pressure wire.

17. A medical information processing system, comprising:
processing circuitry configured to
acquire medical image data representing a coronary artery of a subject;
acquire the medical image data;
extract a blood vessel shape from the medical image data, and determine a deformed region where changes in a Fractional-Flow-Reserve are estimated before and after a deformation of the coronary artery due to insertion of a pressure wire for measuring a Wire-Fractional-Flow-Reserve into the coronary artery, based on the extracted blood vessel shape;
detect a position of the pressure wire in the coronary artery based on the acquired medical image data, and associate the Wire-Fractional-Flow-Reserve measured by the pressure wire with the position of the pressure wire where the Wire-Fractional-Flow-Reserve was measured; and
identifiably display a particular position corresponding to the region in a distribution of the Wire-Fractional-Flow-Reserve by associating the region with the Wire-Fractional-Flow-Reserve associated with the position of the pressure wire.

18. A medical information processing method, comprising:
acquiring medical image data representing a coronary artery of a subject;
extracting a blood vessel shape from the medical image data, and determining a region where changes in a Fractional-Flow-Reserve are estimated before and after a deformation of the coronary artery due to insertion of a pressure wire for measuring a Wire-Fractional-Flow-Reserve into the coronary artery, based on the extracted blood vessel shape;
detecting a position of the pressure wire in the coronary artery based on the acquired medical image data, and associating the Wire-Fractional-Flow-Reserve measured by the pressure wire with the position of the pressure wire where the Wire-Fractional-Flow-Reserve was measured; and identifiably displaying a particular position corresponding to the region in a distribution of the Wire-Fractional-Flow-Reserve by associating the region with the Wire-Fractional-Flow-Reserve associated with the position of the pressure wire.

\* \* \* \* \*